United States Patent
Shim et al.

(10) Patent No.: US 9,655,680 B2
(45) Date of Patent: May 23, 2017

(54) MASTER DEVICES FOR SURGICAL ROBOTS AND CONTROL METHODS THEREOF

(71) Applicant: Samsung Electronics Co., Ltd., Suwon-Si, Gyeonggi-Do (KR)

(72) Inventors: Youngbo Shim, Seoul (KR); Minhyung Lee, Anyang-si (KR); Byungjune Choi, Gunpo-si (KR); Young Do Kwon, Yongin-si (KR); Kyungshik Roh, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 96 days.

(21) Appl. No.: 14/611,725

(22) Filed: Feb. 2, 2015

(65) Prior Publication Data
US 2015/0230869 A1    Aug. 20, 2015

(30) Foreign Application Priority Data
Feb. 18, 2014   (KR) .................. 10-2014-0018505

(51) Int. Cl.
*G06F 19/00*   (2011.01)
*A61B 19/00*   (2006.01)

(52) U.S. Cl.
CPC .. *A61B 19/2203* (2013.01); *A61B 2019/2223* (2013.01); *A61B 2019/2238* (2013.01); *A61B 2019/2242* (2013.01)

(58) Field of Classification Search
USPC ........ 700/245; 606/130; 600/424; 604/95.01
See application file for complete search history.

(56) References Cited

U.S. PATENT DOCUMENTS

| | | | | |
|---|---|---|---|---|
| 5,175,616 A | * | 12/1992 | Milgram | G03B 35/08 |
| | | | | 348/47 |
| 6,468,265 B1 | * | 10/2002 | Evans | A61B 34/32 |
| | | | | 600/103 |

(Continued)

FOREIGN PATENT DOCUMENTS

| | | |
|---|---|---|
| JP | 2009148888 A | 7/2009 |
| KR | 20080047318 A | 5/2008 |

(Continued)

OTHER PUBLICATIONS

Jun. 17, 2015 Extended European Search Report issued in corresponding European Application No. 15154099.4-1659.

*Primary Examiner* — Ronnie Mancho
(74) *Attorney, Agent, or Firm* — Harness, Dickey & Pierce, P.L.C.

(57) ABSTRACT

A master device for surgical robots may comprise: handle units, each of which includes at least one multi-joint robot finger configured to control a robotic surgical instrument on a robot arm of a slave device; and/or a micro motion generation unit configured to generate a control signal to control an end of the at least one multi-joint robot finger so as to move along a virtual trajectory. A master device for surgical robots may comprise: a first unit that comprises at least one multi-joint robot finger on a robot arm of a slave device; and/or a second unit configured to generate a first control signal to control the at least one multi-joint robot finger so as to move along a virtual trajectory.

24 Claims, 13 Drawing Sheets

(56) References Cited

U.S. PATENT DOCUMENTS

| | | | |
|---|---|---|---|
| 6,659,939 B2* | 12/2003 | Moll | A61B 19/2203 600/102 |
| 8,600,551 B2* | 12/2013 | Itkowitz | G09B 23/285 700/245 |
| 9,314,306 B2* | 4/2016 | Yu | A61B 6/12 |
| 2002/0120254 A1* | 8/2002 | Julian | A61B 17/00234 606/1 |
| 2002/0120363 A1 | 8/2002 | Salisbury et al. | |
| 2003/0060927 A1 | 3/2003 | Gerbi et al. | |
| 2004/0024311 A1* | 2/2004 | Quaid, III | A61B 34/20 600/428 |
| 2006/0095022 A1 | 5/2006 | Moll et al. | |
| 2008/0218770 A1* | 9/2008 | Moll | A61G 7/0503 356/614 |
| 2009/0036902 A1* | 2/2009 | DiMaio | A61B 19/2203 606/130 |
| 2011/0238079 A1* | 9/2011 | Hannaford | A61B 19/2203 606/130 |
| 2011/0306986 A1* | 12/2011 | Lee | B25J 9/1689 606/130 |
| 2012/0071891 A1* | 3/2012 | Itkowitz | A61B 19/2203 606/130 |
| 2012/0071892 A1* | 3/2012 | Itkowitz | A61B 19/2203 606/130 |
| 2014/0005687 A1 | 1/2014 | Prisco et al. | |
| 2014/0058406 A1* | 2/2014 | Tsekos | A61B 19/2203 606/130 |
| 2014/0222023 A1* | 8/2014 | Kim | A61B 19/2203 606/130 |
| 2014/0241577 A1* | 8/2014 | Kwak | G06K 9/00624 382/103 |
| 2015/0045812 A1* | 2/2015 | Seo | A61B 19/2203 606/130 |
| 2015/0230869 A1* | 8/2015 | Shim | A61B 19/2203 606/130 |

FOREIGN PATENT DOCUMENTS

| | | |
|---|---|---|
| KR | 20110078226 A | 7/2011 |
| WO | WO 98/51451 | 11/1998 |
| WO | WO 2009/079781 A1 | 7/2009 |

* cited by examiner

MASTER DEVICES FOR SURGICAL ROBOTS AND CONTROL METHODS THEREOF

CROSS-REFERENCE TO RELATED APPLICATION(S)

This application claims priority from Korean Patent Application No. 10-2014-0018505, filed on Feb. 18, 2014, in the Korean Intellectual Property Office (KIPO), the entire contents of which are incorporated herein by reference.

BACKGROUND

1. Field

Some example embodiments of the present disclosure may relate generally to master devices for surgical robots which may generate stable motions of robotic surgical instruments by guiding hand motions of operators. Some example embodiments of the present disclosure may relate generally to control methods thereof.

2. Description of Related Art

In general, minimally invasive surgery means surgery in which the size of an affected part is minimized. Differently from laparotomy performed through a large incision window at a part (the abdomen) of a human body, in minimally invasive surgery, at least one incision hole (or an invasive hole) having a size of 0.5 cm~1.5 cm may be formed at the abdomen, a video camera and various instruments may be put into the abdomen through the incision hole, and then surgery may be performed while watching an image.

Differently from laparotomy, such minimally invasive surgery may cause little pain after surgery, may allow early recovery of intestinal mobility, may allow early feeding of food, may minimize hospitalization time and hasten return to a normal state, and/or may decrease incision ranges to increase beauty effects. Due to these advantages, minimally invasive surgery has been used in cholecystectomy, prostectomy, and hernia repair, and the fields of application of minimally invasive surgery has been increasing.

Surgical robots used in minimally invasive surgery may include master consoles and slave robots (also referred to a slave devices). The master consoles may generate control signals according to operations by operators (e.g., doctors) and/or may transmit the control signals to the slave robots. The slave robots may be operated according to the control signals received from the master consoles. Using the master console, an operator may operate the slave robot even though the slave robot may be located far from the master console. The operator may be in the same room, in a different room, or in a different facility (perhaps located in another country).

The slave robots may be provided with at least one robot arm, and a robotic surgical instrument may be mounted at the front end of each robot arm. The robotic surgical instruments may be inserted into the bodies of patient through incision points. On the other hand, the at least one robot arm may be located outside of the incision points and may serve to maintain the positions and/or poses of the robotic surgical instruments during surgery.

Surgical robots and associated systems provide numerous other advantages, such as potentially improved precision, better ability to monitor the patient, and ability to record the surgical procedure for training, qualification, and/or evidentiary purposes.

Although some example embodiments will be described with relation to surgical robot systems, those skilled in the art will appreciate that some example embodiments may be applied to other types of systems, such as teleoperation systems not used in the medical field (e.g., aerospace teleoperation systems, robots for handling hazardous materials, patrol robots, military robots), or more general purpose control systems.

SUMMARY

Some example embodiments may provide master devices for surgical robots which may generate stable motions of a robotic surgical instruments by guiding hand motions of operators. Some example embodiments may provide control methods for surgical robots which may generate stable motions of a robotic surgical instruments by guiding hand motions of operators.

In some example embodiments, a master device for surgical robots may comprise: handle units, each of which includes at least one multi-joint robot finger configured to control a robotic surgical instrument on a robot arm of a slave device; and/or a micro motion generation unit configured to generate a control signal to control an end of the at least one multi-joint robot finger so as to move along a virtual trajectory.

In some example embodiments, the master device may further comprise: a virtual trajectory generation unit. When information regarding a kind of the robotic surgical instrument is received, the virtual trajectory generation unit may be configured to search a virtual trajectory corresponding to the received kind of the robotic surgical instrument from virtual trajectories that are stored in advance.

In some example embodiments, when at least one of information regarding an operator and information regarding a surgical process is received, the virtual trajectory generation unit may be configured to generate a new virtual trajectory from the searched virtual trajectory based on the at least one received information.

In some example embodiments, the micro motion generation unit may be further configured to generate the control signal to control the end of the at least one multi-joint robot finger so as to move along the new virtual trajectory.

In some example embodiments, the master device may further comprise: wrist support units at positions corresponding to wrists of an operator, the wrist support units configured to rotate the handle units about at least one of an x-axis, a y-axis, and a z-axis; and/or link units operatively connected to the wrist support units and configured to perform translational motion of the wrist support units.

In some example embodiments, the master device may further comprise: a macro motion generation unit configured to generate a control signal to control a pose of the robotic surgical instrument based on rotation information of the wrist support units, and/or configured to generate a control signal to control a position of the robotic surgical instrument based on position information of the wrist support units.

In some example embodiments, the master device may further comprise: a motion fusion unit configured to generate a final motion control signal to control motion of the robotic surgical instrument through fusion between the control signal generated by the micro motion generation unit and the control signal generated by the macro motion generation unit.

In some example embodiments, the motion fusion unit may be further configured to apply weights to the control signal generated by the micro motion generation unit and the control signal generated by the macro motion generation unit.

In some example embodiments, each of the link units may comprise: a first link on which each of the wrist support units is provided; a second link operatively connected to a first end of the first link; a third link operatively connected to a first end of the second link; and/or fourth links operatively connected to a first end of the third link and a second end of the first link. The first link, the second link, the third link, and the fourth links may be configured to form a parallelogram structure.

In some example embodiments, each of the link units may further comprise: a first pulley provided at one side of the first link; a second pulley on a first rotary shaft with which the first link and the fourth links are combined; a third pulley on a second rotary shaft with which the third link and the fourth links are combined; a first cable wound on a first groove of the first pulley, a first groove of the second pulley, and a first groove of the third pulley; and/or a second cable wound on a second groove of the first pulley, a second groove of the second pulley, and a second groove of the third pulley.

In some example embodiments, a first end of the first cable may be fixed to a cable fixing part in the first groove of the first pulley. The first cable may be wound on the first groove of the second pulley in a first direction. A second end of the first cable may be fixed to a cable fixing part in the first groove of the third pulley. A first end of the second cable may be fixed to a cable fixing part in the second groove of the first pulley. The second cable may be wound on the second groove of the second pulley in a second direction. A second end of the second cable may be fixed to a cable fixing part in the second groove of the third pulley.

In some example embodiments, the link units may be further configured to compensate for a length of the first cable and a length of the second cable changed according to rotation of the first to fourth links and, thus, to maintain a pose of the wrist support units.

In some example embodiments, when a current position of the end of the at least one multi-joint robot finger deviates from the virtual trajectory, the micro motion generation unit may be configured to: detect a point on the virtual trajectory having a shortest distance from the current position; adjust an intensity of force applied in a perpendicular direction connecting the detected point and the current position; and/or adjust an intensity of force applied in the tangential direction at the detected point.

In some example embodiments, a control method of a master device for surgical robots, which has handle units, each of which includes at least one multi-joint robot finger configured to control a robotic surgical instrument on a robot arm of a slave device, may comprise: generating a virtual trajectory of an end of the at least one multi-joint robot finger; generating a control signal to control the end of the at least one multi-joint robot finger so as to move along the virtual trajectory; and/or controlling motion of the at least one multi-joint robot finger according to the generated control signal.

In some example embodiments, the generation of the virtual trajectory may include: when information regarding a kind of the robotic surgical instrument is received, searching a virtual trajectory corresponding to the received kind of the robotic surgical instrument from virtual trajectories that are stored in advance; and/or when at least one of information regarding an operator and information regarding a surgical process is received, generating a new virtual trajectory from the searched virtual trajectory based on the at least one received information.

In some example embodiments, the control method may further comprise: generating a control signal to control a pose of the robotic surgical instrument based on rotation information of wrist support units provided at positions corresponding to wrists of the operator and rotating the handle units in a designated axis direction; and/or generating a control signal to control a position of the robotic surgical instrument based on position information of the wrist support units.

In some example embodiments, the generation of the control signal may include: when the current position of the end of the at least one multi-joint robot finger deviates from the virtual trajectory: detecting a point on the virtual trajectory having a shortest distance from the current position; and/or adjusting an intensity of force applied in a perpendicular direction connecting the detected point and the current position, and an intensity of force applied in the tangential direction at the detected point.

In some example embodiments, a master device for surgical robots may comprise: a first unit that comprises at least one multi-joint robot finger on a robot arm of a slave device; and/or a second unit configured to generate a first control signal to control the at least one multi-joint robot finger so as to move along a virtual trajectory.

In some example embodiments, the master device may further comprise: a third unit corresponding to a wrist of an operator. The third unit may be configured to rotate the first unit about at least one of an x-axis, a y-axis, and a z-axis.

In some example embodiments, the master device may further comprise: a fourth unit configured to generate a second control signal to control the robot arm based on rotation information of the third unit.

In some example embodiments, the master device may further comprise: a fifth unit configured to generate a third control signal to control the robot arm based on the first and second control signals.

In some example embodiments, the master device may further comprise: a fourth unit configured to generate a second control signal to control the robot arm based on position information of the third unit.

In some example embodiments, the master device may further comprise: a fifth unit configured to generate a third control signal to control the robot arm based on the first and second control signals.

In some example embodiments, the master device may further comprise: a fourth unit configured to generate a second control signal to control the robot arm based on rotation information and position information of the third unit.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
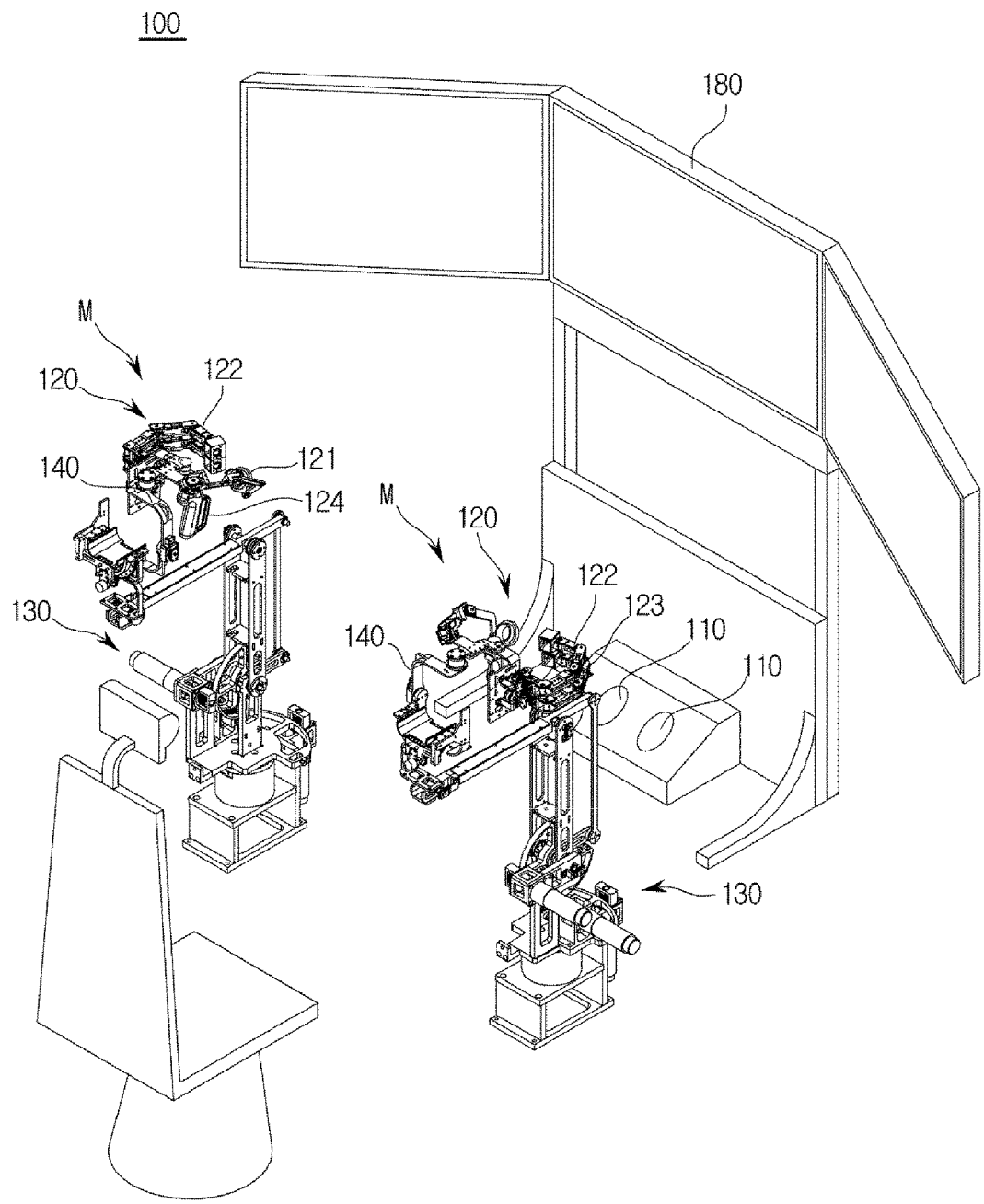
FIG. 1 is a perspective view exemplarily illustrating the external appearance of a master console of a surgical robot.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Some example embodiments of the present disclosure may be applied to single-port and/or multi-port surgical robots. Multi-port surgical robots may refer to robots configured to insert a plurality of robotic surgical instruments into the abdominal cavities of patients through individual invasion sites. On the other hand, single-port surgical robots may refer to robots configured to insert a plurality of robotic surgical instruments into the abdominal cavities of patients through one invasion site.

Figure 2:
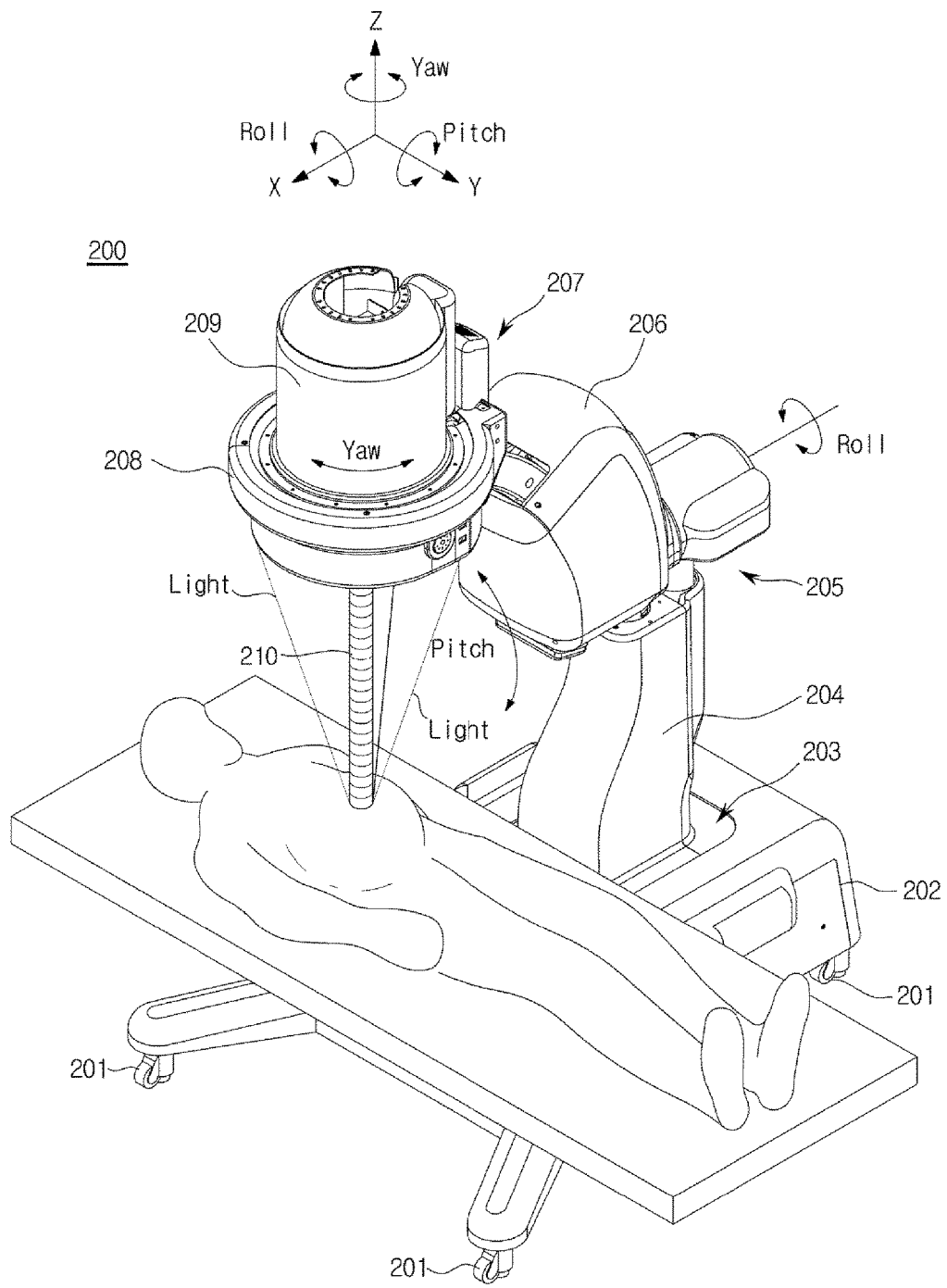
FIG. 2 is a perspective view exemplarily illustrating the external appearance of a slave robot of the surgical robot.

The surgical robot includes a master console 100 (in FIG. 1) and a slave robot 200 (in FIG. 2). The master console 100 is a device having a remote control function of the slave robot 200. The master console 100 transmits a control signal according to operation of an operator to the slave robot 200. The slave robot 200 receives the control signal from the master console 100. Then, the slave robot 200 moves according to the received control signal, and applies operations required for surgery to a patient. In some example embodiments, the operator may be one or more medical personnel, such as a medical specialist or a doctor. Otherwise, the operator may include a person having qualifications equivalent to medical personnel or a granted person. Broadly, the operator may include a user controlling operation of the surgical robot.

In some example embodiments, the master console 100 may not be a single device, but may include more than one device, each performing one or more functions of the master console 100. Thus, in some example embodiments, the functionality of the master console 100 may be distributed.

Similarly, in some example embodiments, the slave robot 200 may not be a single robot, but may include more than one robot, each performing one or more functions of the slave robot 200. Thus, in some example embodiments, the functionality of the slave robot 200 may be distributed.

Therefore, in some example embodiments, the functionality of the master console 100, the slave robot 200, or the master console 100 and the slave robot 200 may be distributed.

In some example embodiments, the master console 100 may be required to perform certain functions, but may or may not perform other functions while maintaining its role as the master console 100. One or more of these other functions may be shared with or performed by the slave robot 200 (which maintains its role as the slave robot 200). Similarly, in some example embodiments, the slave robot 200 may be required to perform certain functions, but may or may not perform other functions while maintaining its role as the slave robot 200. One or more of those other functions may be shared with or performed by the master console 100 (which maintains its role as the master console 100).

Therefore, in some example embodiments, the required functionality of the master console 100 and the slave robot 200 may be maintained, while functionality that may be shared with or performed by the other device/robot may be so shared with or performed by the other device/robot consistent with the master console 100 maintaining its role as the master console 100 and the slave robot 200 maintaining its role as the slave robot 200.

FIG. 1 is a view illustrating the external appearance of the master console 100 of a surgical robot.

As exemplarily shown in FIG. 1, the master console 100 may include an input unit and displays 180.

The input unit receives instructions to remotely operate the slave robot 200 (in FIG. 2) from an operator(s). For example, the input unit may include at least one of master devices M and clutch pedals 110. FIG. 1 exemplarily illustrates the input unit as including two clutch pedals 110 and two master devices M. Master devices M may facilitate surgical procedures by more than one doctor simultaneously.

The clutch pedals 110 may be used to switch between operation modes of the surgical robot. For example, if the left clutch pedal 110 is operated, a guide tube operation mode may be performed, and if the right clutch pedal 110 is operated, a robotic surgical instrument operation mode may be performed. When the guide tube operation mode is performed, the operator may change the position and pose of a guide tube 210 (in FIG. 2) by operating the master devices M. Further, when the robotic surgical instrument operation mode is performed, movement of the guide tube 210 is stopped and the operator may change the positions and poses of robotic surgical instruments 212 and 214 (in FIG. 3) by operating the master devices M.

The master devices M remotely control movement of a robot arm 203~208 (in FIG. 2) or robotic surgical instruments 212, 214, and 216 provided on the slave robot 200 (in FIG. 2). The master device M may include a handle unit 120, a wrist support unit 140 mechanically connected to the handle unit 120, a link unit 130 mechanically connected to the wrist support unit 140, and a support unit 150 mechanically connected to the link unit 130 and causing the link unit 130 to be supported by the ground.

The handle units 120 may be implemented as haptic devices. The haptic devices may include, for example, at least one multi-joint robot finger. The at least one multi-joint robot finger may be disposed in a shape similar to that of a human hand. FIG. 1 illustrates that three multi-joint robot fingers 121, 122, and 123 are provided at positions corresponding to the thumb, the forefinger, and the middle finger of a human hand.

Although FIG. 1 illustrates the handle units 120 as including three multi-joint robot fingers 121, 122, and 123, the number and positions of the multi-joint robot fingers provided on the handle units 120 are not limited thereto. For example, the handle units 120 may be provided with multi-joint robot fingers smaller or greater in number than three, and these multi-joint robot fingers may be provided at positions corresponding to at least one of the thumb, the index finger, the middle finger, the ring finger, and the little finger of a human hand.

Further, the multi-joint robot fingers provided on one handle unit 120 may have the same shape or different shapes. With reference to FIG. 1, it may be understood that the multi-joint robot fingers 122 and 123 provided at positions corresponding to the index finger and the middle finger of a human hand have the same shape. On the other hand, it may be understood that the multi-joint robot finger 121 provided at a position corresponding to the thumb of the human hand has a shape differing from the shape of the multi-joint robot fingers 122 and 123. Hereinafter, the multi-joint robot finger 122 corresponding to the index finger of the human hand will be described.

The multi-joint robot finger 122 may include plural links and plural joints. In some example embodiments, the joint means a connection region between one link and another link. The joint may have at least 1 degree of freedom (DOF). DOF denotes DOF in forward kinematics or inverse kinematics.

The DOF of a mechanism refers to the number of independent movements of the mechanism or the number of variables determining independent movements of relative positions of respective links. For example, an object in three dimensional (3D) space formed by the x-axis, the y-axis, and the z-axis has at least 1 DOF from among 3 DOF to determine the spatial position of the object (positions of the object on the respective axes) and 3 DOF to determine the spatial orientation of the object (rotation angles of the object about the respective axes). In more detail, it may be understood that if the object is movable along the respective axes and is rotatable about the respective axes, the object has 6 DOF.

A detection unit to detect information regarding the state of each joint may be provided at each joint of the multi-joint robot finger 122. In some example embodiments, the detection unit may include a position detection unit to detect the position of each joint (e.g., a joint angle), and a velocity detection unit to detect the velocity of each joint. According to circumstance, the velocity detection unit may be omitted. If the velocity detection unit is omitted, the velocity of the joint may be acquired by differentiating the position detected by the position detection unit.

The front end of the multi-joint finger 122 may be understood as an end effector of the master console 100. For example, a thimble-type loop may be provided at the front end of the multi-joint robot finger 122. The operator may insert his/her finger into the thimble-type loop. If the operator moves the finger under the condition that the finger is inserted into the thimble-type loop, the multi-joint robot finger 122 moves so as to correspond to movement of the finger of the operator, and the detection units provided at the respective joints of the multi-joint robot finger 122 may detect information regarding the states of the respective joints.

Further, a tactile feedback actuator 125 (in FIG. 8) may be provided at the thimble-type loop. If the robotic surgical instrument inserted into the abdomen of a patient contacts external environment, for example, an organ, force received by the robotic surgical instrument from the external environment is transmitted to the tactile feedback actuator 125. As a result, the operator may indirectly feel force received by the robotic surgical instrument from the external environment.

The positions and velocities of the respective joints detected through the respective detection units may be converted into target positions and target velocities which the respective joints of the robotic surgical instruments will follow. The converted target positions and target velocities may be transmitted to the slave robot 200 (in FIG. 2) through a network. In some example embodiments, the network may be a wired network, a wireless network, or a wired/wireless hybrid network.

Although FIG. 1 illustrates the handle units 120 as being provided with the haptic devices including the plural multi-joint robot fingers 121, 122, and 123, the shape of the haptic devices provided on the handle units 120 is not limited thereto. As one example, the handle units 120 may be implemented as haptic devices having a pencil shape or a stick shape so that the operator may grasp the haptic devices by hand. As another example, the handle units 120 may be implemented as haptic devices having a scissors shape so that the operator may insert at least two fingers into the handle unit 120. As yet another example, the handle units 120 may be implemented as haptic devices having a glove shape so that the operator may insert all fingers into the handle unit 120.

Although FIG. 1 illustrates a plurality of handle units 120 as being implemented as haptic devices including at least one multi-joint finger, example embodiments of the present disclosure are not limited thereto. According to some example embodiments of the present disclosure, a plurality of handle units 120 may be implemented as haptic devices having different shapes. For example, one handle unit 120 may be implemented as a haptic device having a scissors shape, and another handle unit 120 may be implemented as a haptic device including at least one multi-joint robot finger.

The wrist support units 140 are arranged at positions corresponding to the wrists of the operator. The wrist support units 140 may have various shapes. As one example, the wrist support units 140 may have a circular shape. In this case, the operator may put the hands into the wrist support units 140 and, then, insert the tip of the least one finger of each hand into the thimble-type loop provided at the front end of the multi-joint robot finger.

As another example, the wrist support units 140 may have a semicircular shape, as exemplarily shown in FIG. 1. In this case, opened regions of the semicircular wrist support units 140 may be disposed so as to face the inside of the master console 100 (e.g., the body of the operator), and closed regions of the semicircular wrist support units 140 may be disposed so as to face the outside of the master console 100. Otherwise, the curved regions of the semicircular wrist support parts 140 may be disposed so as to face the ground. Force/torque (F/T) detection units may be provided at the wrist support units 140. The F/T detection units detect forces applied to the handle units 120 by the operator. The F/T detection units may be, for example, multi-axis force/torque (F/T) sensors.

One end of the link unit 130 is mechanically connected to the wrist support unit 140. The other end of the link unit 130 is combined with the upper portion of a support frame 137. The support frame 137 is mechanically connected to the upper portion of the support unit 150. The support unit 150 is fixed to the ground. The support frame 137 may be rotated about a coupling axis of the support unit 150.

The link units 130 may include a plurality of links. A joint is provided between a link and another link. Such a joint may have at least 1 DOF. A more detailed description of the structure and operating principle of the link units 130 will be given later with reference to FIGS. 4 to 7.

FIG. 1 illustrates that the other end of the link unit 130 is connected to the upper portion of the support frame 137. However, the structure of the link unit 130 is not limited thereto. For example, differing from FIG. 1, the other end of the link unit 130 may be connected to a chair.

At least one of the handle units 120, the link units 130, and the pedals 110 may be additionally provided with a communication unit (not shown) to transmit and receive control signals and/or data through wired communication or wireless communication with the slave robot 200.

Displays 180 display at least one of image data and surgical information. The image data displayed through the displays 180 may be an image captured by an endoscope 216a (in FIG. 3) of the slave robot 200, or be acquired through image processing of the captured image. Image processing may include at least one of image enlargement, reduction, movement, rotation, combination with another image, and filtering. Such image processing may be performed by at least one of the slave robot 200 and the master console 100. Surgical information displayed through the displays 180 may include biometric information of a patient. For example, the biometric information may be temperature, pulse, respiration, and blood pressure.

One or more displays 180 may be provided. For example, the monitors may support stereoscopic viewing or viewing from multiple angles at the same time. Although FIG. 1 illustrates three displays 180 disposed in the horizontal direction in parallel on the master console 100, the number of monitors may vary according to type or kind of information to be displayed.

As one example, plural displays 180 may display different images. In more detail, a main display located in front of the operator may display an image captured by the endoscope. Sub-displays located at the left and right of the main display may display information regarding the operating state of the slave robot and patient information, respectively.

As another example, the plural displays 180 may display the same image. In this case, the same image may be displayed through the respective displays 180, or one image may be displayed through the entirety of the plural displays 180. In addition, current images may be compared to or blended with previous images to facilitate analysis and/or action with regard to the patient.

For example, the above-described displays 180 may be implemented as liquid crystal displays (LCDs), light emitting diodes (LEDs), organic light emitting diodes (OLEDs), plasma display panels (PDPs), or combinations thereof.

FIG. 2 is a perspective view exemplarily illustrating the external appearance of the slave robot 200 of the surgical robot.

As exemplarily shown in FIG. 2, the slave robot 200 includes casters 201, a body 202, the robot arm 203~208, and a surgical instrument assembly 209.

The casters 201 serve to move the slave robot 200, and may be mounted at the lower end of the body 202. At least one caster 201 may be mounted at the lower end of the body 202. A lever (not shown) to change the operating state of each caster may be provided at each caster. The operator may change the operating states of the casters 201 by adjusting the positions of the levers. The operating states of the casters 201 may include a brake state, a free-swivel state, and a directional lock (or swivel-lock) state.

The robot arm 203~208 is provided at the upper part of the body 202. The robot arm 203~208 moves the surgical instrument assembly 209 along at least one of the x-axis, the y-axis, and the z-axis, or rotates the surgical instrument assembly 209 about at least one of the x-axis, the y-axis, and the z-axis. Further, the robot arm 203~208 supports the surgical instrument assembly 209 so that the position and pose of the surgical instrument assembly 209 may be maintained during surgery.

The robot arm 203~208 may include plural link units 204, 206, and 208, and plural joint units 203, 205, and 207. In more detail, the robot arm 203~208 may include a first joint unit 203, a first link unit 204, a second joint unit 205, a second link unit 206, a third joint unit 207, and a third link unit 208.

The first link unit 204 may include a first link and a casing surrounding the first link. The first link may have a rectilinear column shape and be provided in the direction perpendicular to the body 202. In some example embodiments, the first link may be provided in the direction perpendicular to the ground.

The first joint unit 203 is provided at the connection region between the body 202 and the first link unit 204. The first joint unit 203 may be implemented as a prismatic joint moving along a designated axis or axes from among the x-axis, the y-axis, and the z-axis. The first joint unit 203 serves to perform translational motion of the surgical instrument assembly 209, and has 3 DOF. In more detail, the first joint unit 203 has 3 DOF including x-axis translation, y-axis translation, and z-axis translation. For this purpose, the first joint unit 203 includes an x-axis translational drive unit, a y-axis translational drive unit, and a z-axis translational drive unit. Although not shown in FIG. 2, each translational drive unit may include a linear motion guide guiding linear motion along a specific axis and a motor providing driving force to the linear motion guide.

The second link unit 206 is provided at the front end of the first link unit 204. The second link unit 206 includes a second link and a casing surrounding the second link. The second link has a curved shape. In more detail, the second link has a shape of a part of an arc.

The second joint unit 205 is provided at the connection region between the first link unit 204 and the second link unit 206. The second joint unit 205 may be implemented as a revolute joint rotating about a designated axis or axes from among the x-axis, the y-axis, and the z-axis. The second joint unit 205 serves to perform rotary motion of the surgical instrument assembly 209, and has 2 DOF. In more detail, the second joint unit 205 has 2 DOF including rotation of the surgical instrument assembly 209 in the roll direction and rotation of the surgical instrument assembly 209 in the pitch direction. For this purpose, the second joint unit 205 may include a roll drive unit and a pitch drive unit.

When driving force is provided to the roll drive unit, the second link unit 206 is rotated in the roll direction. As the second link unit 206 is rotated in the roll direction, the third link unit 208 and the surgical instrument assembly 209 provided at the front end of the second link are rotated in the roll direction. For example, the roll drive unit may be one of a motor, a vacuum pump, and a hydraulic pump.

The pitch drive unit may include an R guide guiding arc motion of the second link, and a motor providing driving force to the R guide. When the motor of the pitch drive unit is driven, the second link moves along the R guide. As a result, the third link unit 208 and the surgical instrument assembly 209 provided at the front end of the second link are rotated in the pitch direction.

The third link unit 208 is provided at the front end of the second link unit 206. The third link unit 208 may include a third link having a circular shape. The surgical instrument assembly 209 is provided on the third link. A plurality of light emitting units to indicate a remote center of motion (RCM) point is provided at the lower end of the third link. FIG. 2 illustrates that three light emitting units are provided.

The plural light emitting units may be arranged at the same interval along the circumference of the third link. The plural light emitting units serve to indicate the RCM point and may thus, be implemented as light emitting devices emitting light in a specific direction, for example, laser beams.

Laser beams emitted from the plural light emitting units intersect at the RCM point. When the robot arm 203~208 moves in at least one of the x-axis direction, the y-axis direction, and the z-axis direction, and the RCM point coincides with an incision site of a patient, the guide tube 210 is inserted into the incision site of the patient. Next, robotic surgical instruments provided within the surgical instrument assembly 209 are inserted into the incision site of the patient along (e.g., from within) the guide tube 210. Thereafter, the robotic surgical instruments may be controlled so as to move within a conical workspace using the RCM point as an apex. When the robotic surgical instruments are controlled in such a manner, even if an unexpected movement of the robot arm 203~208 located at the outside of the incision site occurs, damage to the incision site may be prevented.

The third joint unit 207 is provided at the connection region between the second link unit 206 and the third link unit 208. The third joint unit 207 may be implemented as a revolute joint rotating about a designated axis or axes from among the x-axis, the y-axis, and the z-axis. The third joint unit 207 serves to perform rotary motion of the surgical instrument assembly 209, and has 1 DOF. In more detail, the third joint unit 207 has 1 DOF including rotation of the surgical instrument assembly 209 in the yaw direction. For this purpose, the third joint unit 207 may include a yaw drive unit.

When driving force is provided to the yaw drive unit, the surgical instrument assembly 209 is rotated in the yaw direction. The yaw drive unit may be one of a motor, a vacuum pump, and a hydraulic pump.

The surgical instrument assembly 209 may include a cylindrical casing, plural robotic surgical instruments provided along the inner surface of the casing, and the guide tube 210. Further, the robotic surgical instruments may include an endoscope 216a (in FIG. 3) to capture an image of the inside of the abdominal cavity and surgical instruments 212 and 214 (in FIG. 3) to resect, cauterize, and coagulate human body tissues. Among the plural robotic surgical instruments provided along the inner surface of the casing, at least one robotic surgical instrument selected by the operator may be inserted into the abdominal cavity of a patient through the guide tube 210. A detailed description of the robotic surgical instruments will be given later with reference to FIG. 3.

The surgical instrument assembly 209 may be mechanically separated from the third link unit 208. If the surgical instrument assembly 209 is separated from the third link unit 208, it may be easy to replace or disinfect a surgical instrument used in surgery.

Figure 3:
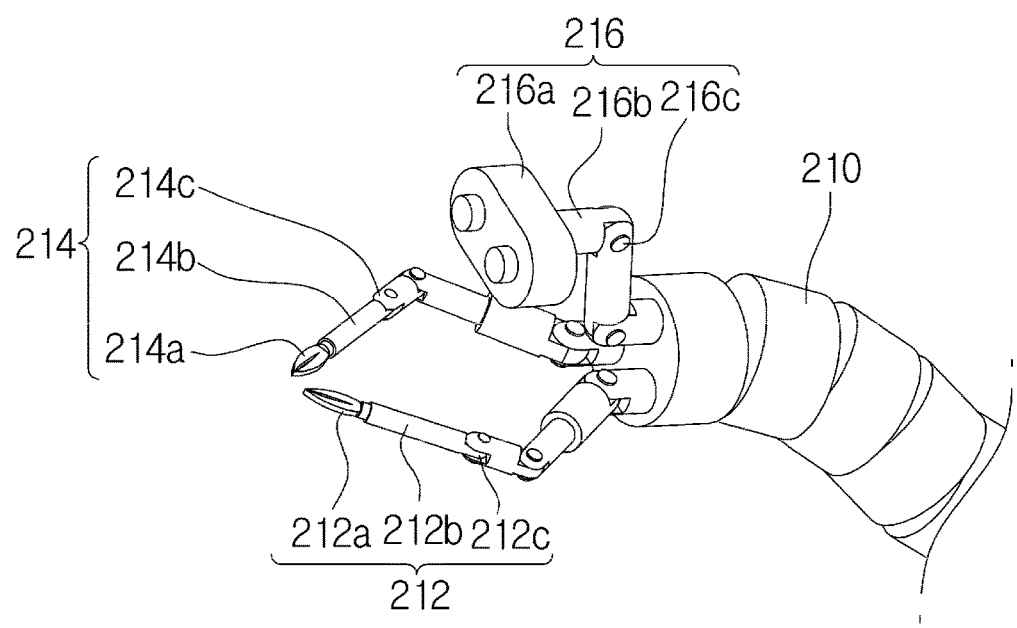
FIG. 3 is a view exemplarily illustrating robotic surgical instruments spread through a guide tube.

FIG. 3 is a view exemplarily illustrating the robotic surgical instruments 212, 214, and 216, spread through the guide tube 210.

As described above, at least one robotic surgical instrument 212, 214, or 216 is inserted into the abdominal cavity of a patient along (e.g., from within) the guide tube 210. Entry of the at least one robotic surgical instrument 212, 214, or 216 into the abdominal cavity of the patient may be performed through various methods. As one example, the guide tube 210 may be inserted into the abdominal cavity of the patient, and then movement of the guide tube 210 may be fixed. Next, the at least one robotic surgical instrument 212, 214, or 216 may be inserted into the guide tube 210, and then move along the inner wall of the guide tube 210. As another example, the at least one robotic surgical instrument 212, 214, or 216 may be inserted into the guide tube 210, and the guide tube 210 in such a state may enter into the abdominal cavity of a patient.

When the guide tube 210 reaches a target position, the at least one robotic surgical instrument 212, 214, or 216 is spread to the outside of the guide tube 210, as exemplarily shown in FIG. 3. FIG. 3 illustrates spreading of three robotic surgical instruments 212, 214, and 216 to the outside of the guide tube 210.

The respective robotic surgical instruments 212, 214, and 216 may include a plurality of links 212b, 214b, and 216b, and a plurality of joints 212c, 214c, and 216c.

An endoscope 216a and surgical tools 212a and 214a are provided at the tips of the respective links 212b, 214b, and 216b. The endoscope 216a and the surgical tools 212a and 214a may be understood as being end effectors of the slave robot 200.

The joints 212c, 214c, and 216c are provided between one link and another link. Each of the above-described joints 212c, 214c, and 216c may be one of a fixed joint, a revolute joint rotating about a designated axis or axes from among the x-axis, the y-axis, and the z-axis, and a prismatic joint linearly moving along a designated axis or axes from among the x-axis, the y-axis, and the z-axis. These joints 212c, 214c, and 216c may have 1 or more DOF.

A drive unit may be provided at each of the joints 212c, 214c, and 216c of the robotic surgical instruments 212, 214, and 216. The drive unit is driven according to a control signal received from the master console 100 and moves the corresponding joint. The drive unit may be implemented as one of a motor, a vacuum pump, and a hydraulic pump. Hereinafter, the case in which a motor is used as the drive unit will be exemplarily described.

A detection unit is provided at each of the joints 212c, 214c, and 216c of the robotic surgical instruments 212, 214, and 216. The detection unit may include a position detection unit to detect the position of each joint (e.g., a joint angle) and a velocity detection unit to detect the velocity of each joint.

As above, the external appearances of the master console 100 and the slave robot 200 of the surgical robot in accordance with some example embodiments have been described. Hereinafter, the master device M provided in the master console 100 will be described in more detail with reference to FIGS. 4 to 11.

Figure 4:
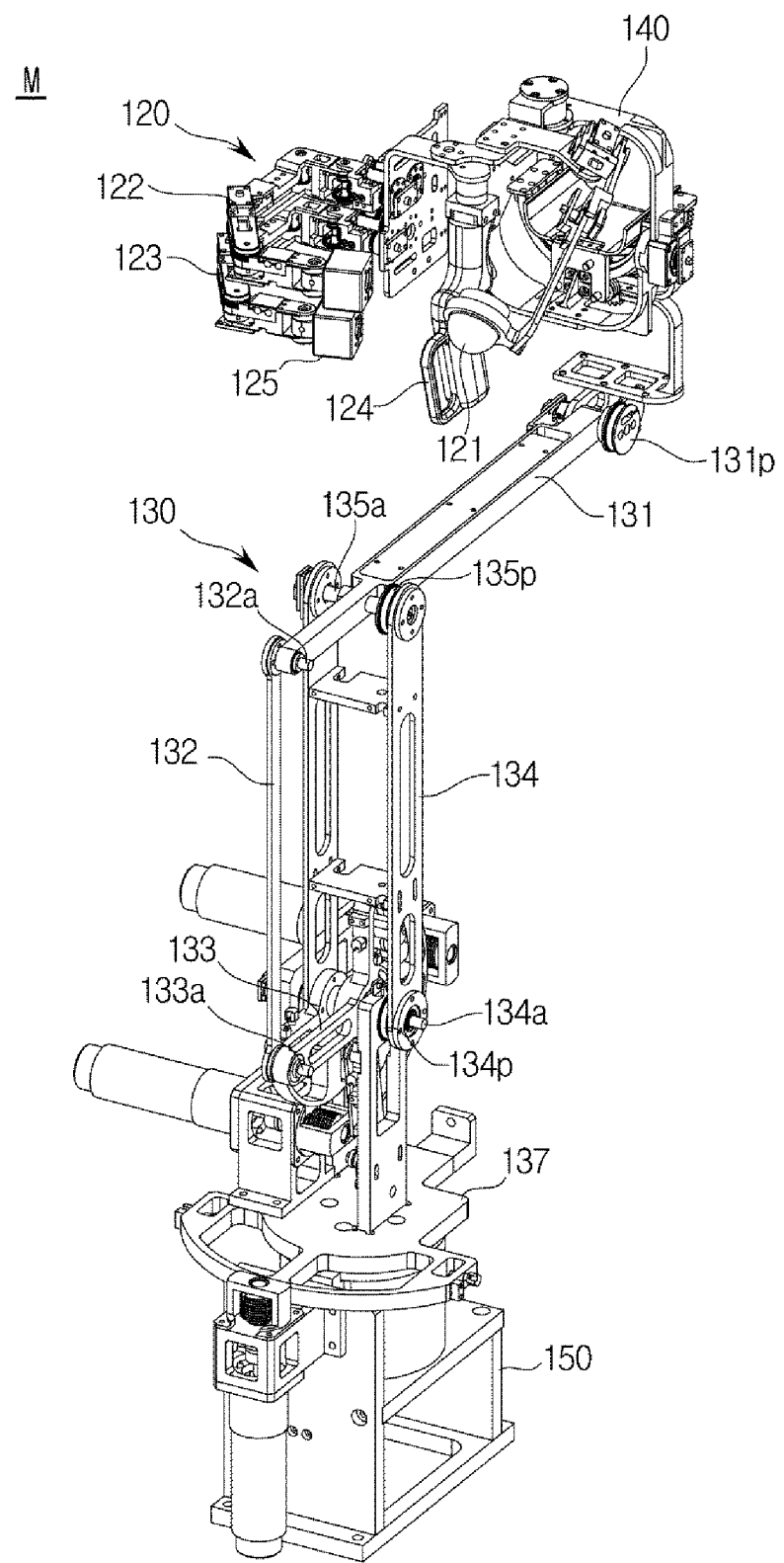
FIG. 4 is a view exemplarily illustrating the external appearance of a master device corresponding to a right hand of an operator among two master devices provided on the master console.
Figure 5:
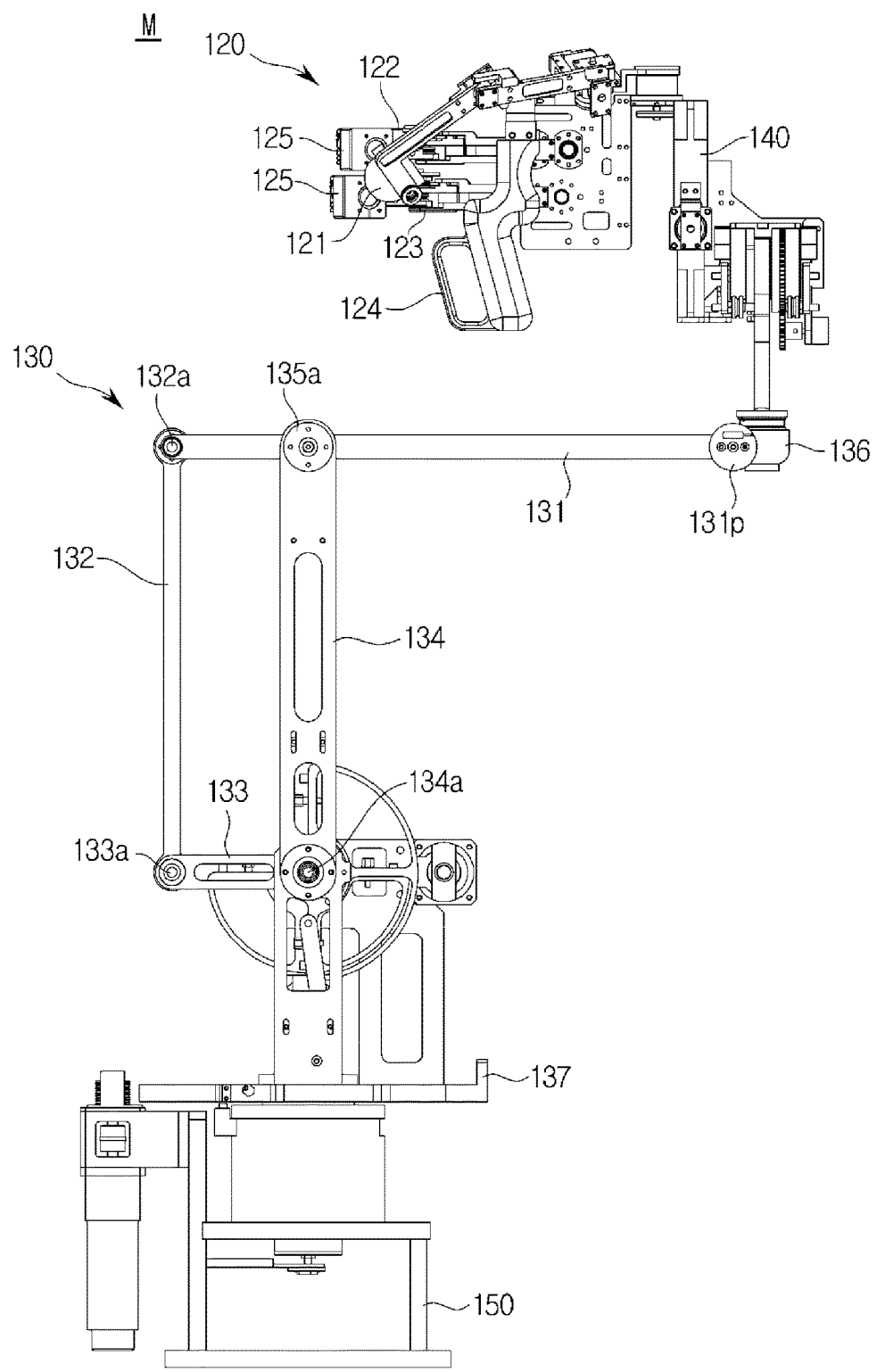
FIG. 5 is a side view of the master device.

FIG. 4 is a view exemplarily illustrating the external appearance of the master device M corresponding to a right hand of an operator among two master devices provided on the master console, and FIG. 5 is a side view of the master device M shown in FIG. 4.

With reference to FIGS. 4 and 5, the master device M may include the handle unit 120, the wrist support unit 140, the link unit 130, and the support unit 150.

The handle unit 120 may include three multi-joint robot fingers 121, 122, and 123 and a handle 124. The multi-joint robot fingers 121, 122, and 123, for example, may be provided at positions corresponding to the thumb, the forefinger, and the middle finger of a human hand. The handle 124, for example, may be provided at a position corresponding to the ring finger and the little finger of a human hand. An operator may grip the handle 124 using his/her ring finger and little finger.

The plural multi-joint robot fingers 121, 122, and 123 and the handle 124 may be mechanically connected to the wrist support unit 140. The wrist support unit 140 may be provided at a position corresponding to an operator's wrist. The wrist support unit 140 serves to rotate the handle unit 120 and may have 3 DOF. For example, the wrist support unit 140 may rotate the handle unit 120 about the x-axis, the y-axis, or the z-axis. A 3-axis force/torque sensor may be provided at the wrist support unit 140.

The wrist support unit 140 may be mechanically connected to the link unit 130. The link unit 130 serves to perform translational motion of the wrist support unit 140 and may have 3 DOF. For example, the link unit 130 may move the wrist support unit 140 along the x-axis, the y-axis, or the z-axis.

The link unit 130 may include a plurality of links 131, 132, 133, and 134. In more detail, the link unit 130 may include a first link 131, a second link 132, a third link 133, and a pair of fourth links 134. As the master device M is seen from the side, the first to fourth links 131, 132, 133, and 134 may be arranged to form a parallelogram.

In more detail, with reference to FIG. 5, the first link 131, for example, may be arranged in parallel with the ground. An end effector 136 may be provided at one end of the first link 131. The wrist support unit 140 and the handle unit 120 may be provided above the end effector 136. A first pulley 131p may be provided at a portion of the end of the first link 131 corresponding to the inner part of the wrist of the operator.

One end of the second link 132 is combined with the other end of the first link 131 by a rotary shaft 132a. In some example embodiments, the second link 132 may be arranged perpendicular to the first link 131. The second link 132 connected to the other end of the first link 131 may rotate about the rotary shaft 132a.

One end of the third link 133 is combined with the other end of the second link 132 by a rotary shaft 133a. The third link 133 may be arranged in parallel with the first link 131. The length of the third link 133 may be less than the length of the first link 131. The third link 133 connected to the other end of the second link 132 may rotate about the rotary shaft 133a.

A pair of fourth links 134 may be arranged between the first link 131 and the third link 133. The length of the pair of fourth links 134 may be equal to the length of the second link 132. The pair of fourth links 134 is arranged opposite each other.

The first link 131 is arranged between one end of one fourth link 134 and one end of another fourth link 134. The ends of the pair of fourth links 134 and the first link 131 arranged between the ends of the pair of the fourth links 134 are combined by a rotary shaft 135a. The first link 131 may rotate about the rotary shaft 135a. A second pulley 135p is provided on the rotary shaft 135a. In more detail, the second pulley 135p is arranged on the rotary shaft 135a opposite the first pulley 131p.

The third link 133 is arranged between the other end of one fourth link 134 and the other end of another fourth link 134. The other ends of the pair of fourth links 134 and the third link 133 arranged between the other ends of the pair of the fourth links 134 are combined by a rotary shaft 134a. The third link 133 may rotate about the rotary shaft 134a. A third pulley 134p is provided on the rotary shaft 134a. In more detail, the third pulley 134p is arranged on the rotary shaft 134a opposite the second pulley 135p.

Each of the first pulley 131p, the second pulley 135p, and the third pulley 134p may have a dual groove structure. In each pulley, two grooves may be connected or separated by a designated interval.

Among the two grooves of each of the first pulley 131p, the second pulley 135p, and the third pulley 134p, a groove located at the outer part of a wrist is referred to as a first groove and a groove located at the inner part of the wrist is referred to a second groove. A first cable may be wound on the first groove of each of the first pulley 131p, the second pulley 135p, and the third pulley 134p, and a second cable may be wound on the second groove of each of the first pulley 131p, the second pulley 135p, and the third pulley 134p.

In more detail, one end of the first cable is fixed to a cable fixing part provided in the first groove of the first pulley 131p. Further, the other end of the first cable is wound on the first groove of the second pulley 135p and is then fixed to a cable fixing part provided in the first groove of the third pulley 134p. The first cable also may be wound and fixed in a different sequence, as would be understood by a person having ordinary skill in the art (PHOSITA).

In a similar manner, one end of the second cable is fixed to a cable fixing part provided in the second groove of the first pulley 131p. Further, the other end of the second cable is wound on the second groove of the second pulley 135p and is then fixed to a cable fixing part provided in the second groove of the third pulley 134p. The second cable also may be wound and fixed in a different sequence, as would be understood by a PHOSITA.

In some example embodiments, the winding direction of the second cable on the second groove of each of the pulleys 131p, 134p, and 135p may be opposite to the winding direction of the first cable on the first groove of each of the pulleys 131p, 134p, and 135p.

Figure 6A:
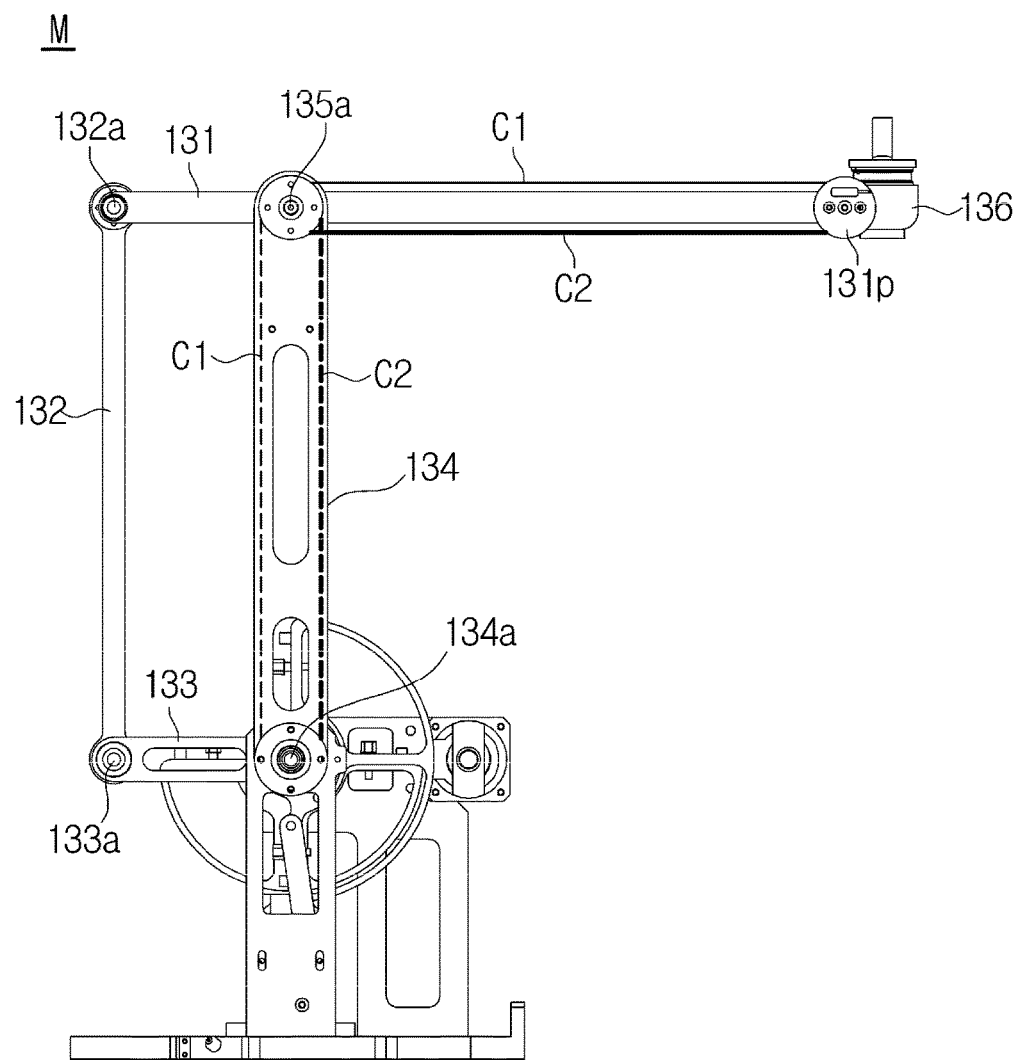
FIGS. 6A, 6B, and 6C are side views of a link unit of the master device, illustrating motion of the link unit.
Figure 6B:
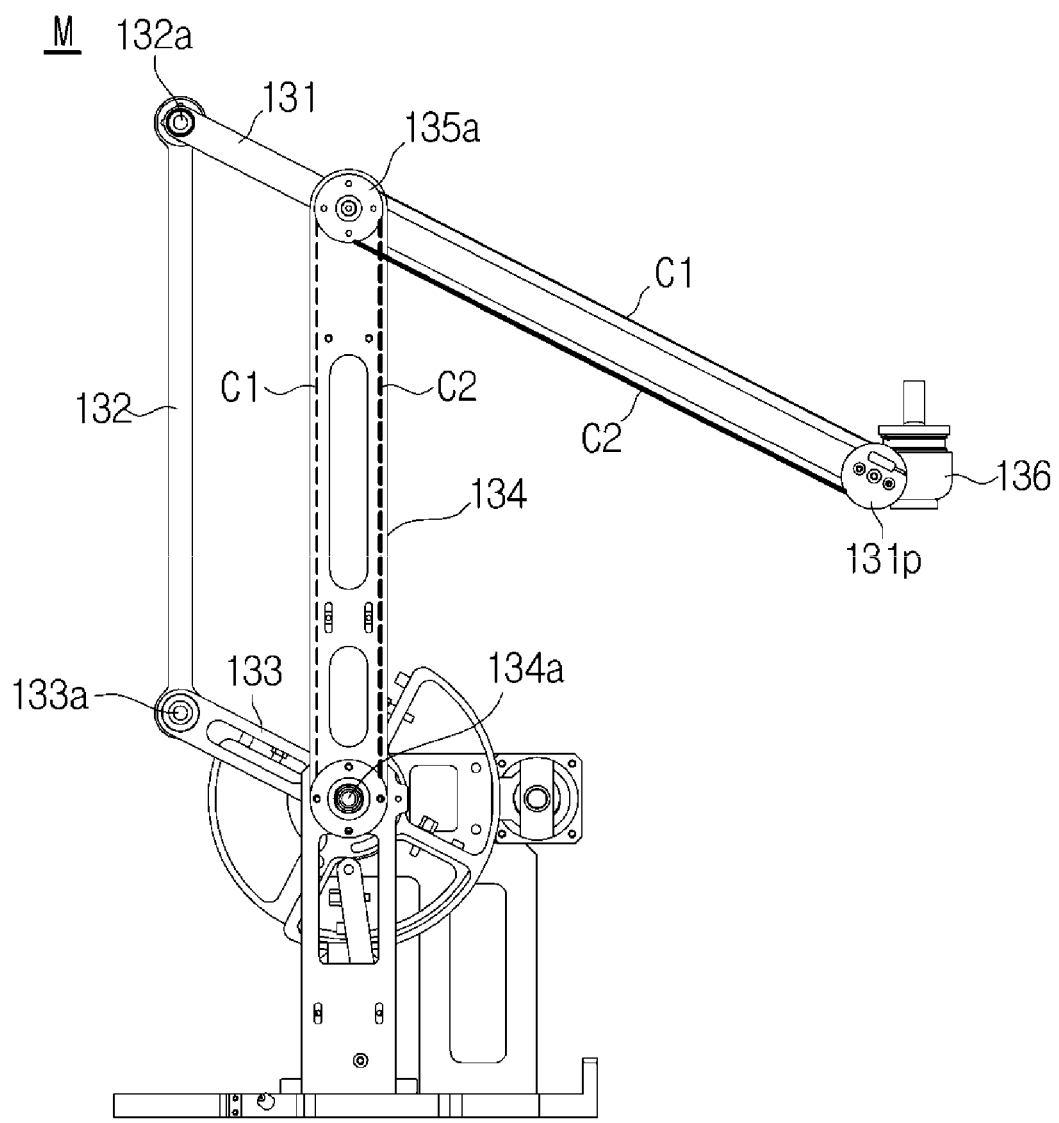
Figure 6C:
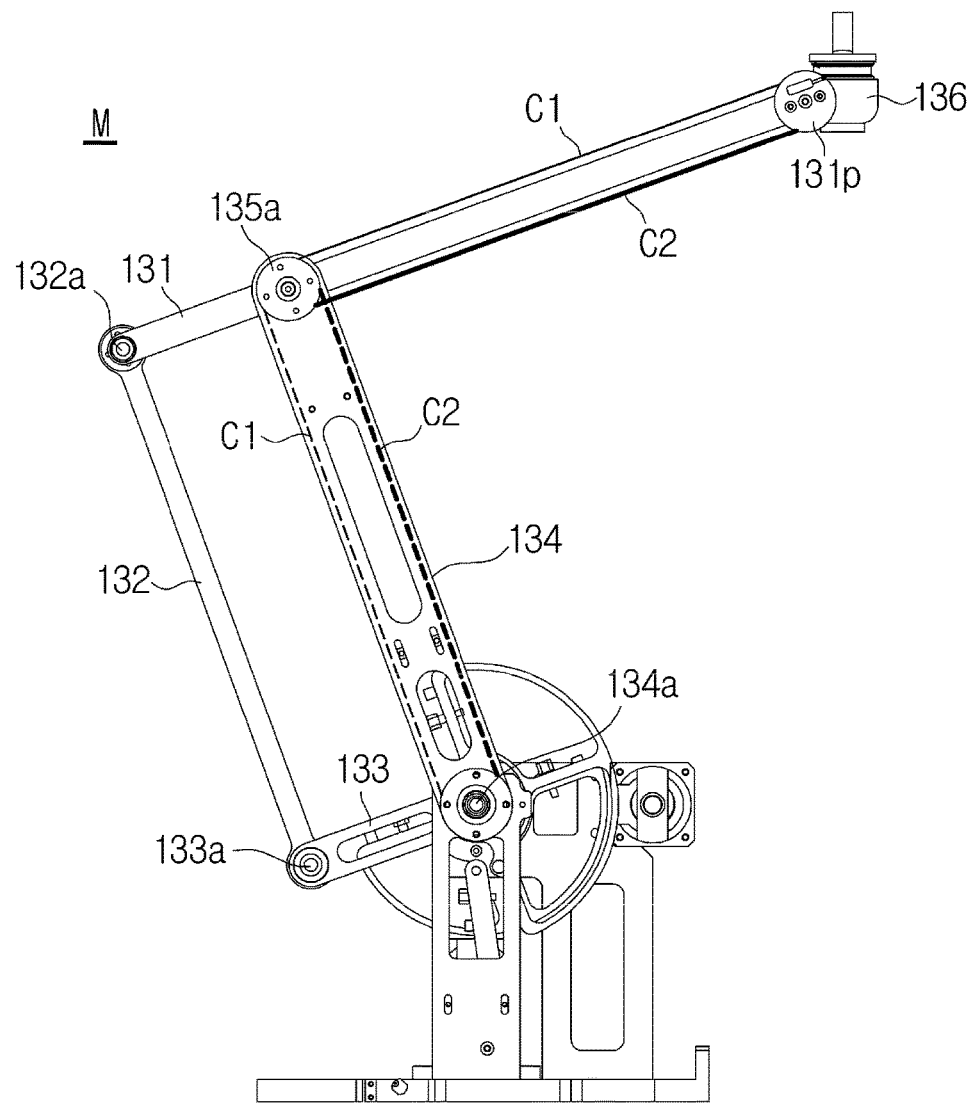

If the plurality of pulleys 131p, 134p, and 135p and the plural cables are used in such a manner, although the position of the end effector 136 is changed, as exemplarily shown in FIGS. 6A-6C, the end effector 136 may maintain a pose horizontal with the ground at all times. Since the end effector 136 maintains the horizontal pose at all times, the wrist support unit 140 and the handle unit 120 provided above the end effector 136 may maintain the horizontal pose at all times.

As described above, the structure of the master device M has been described with reference to FIGS. 4, 5, and 6A-6C. The case that the link unit 130 has a one-axis structure has been described. However, the structure of the link unit 130 is not limited thereto. For example, the link unit 130 may have a multi-axis structure. Although the link unit 130 has a multi-axis structure, the end effector 136 may maintain the pose horizontal with the ground at all times. Hereinafter, a more detailed description of a principle of maintaining the pose of the end effector 136 in the link unit 130 having a multi-axis structure will be given with reference to FIGS. 7A-7C.

Figure 7A:
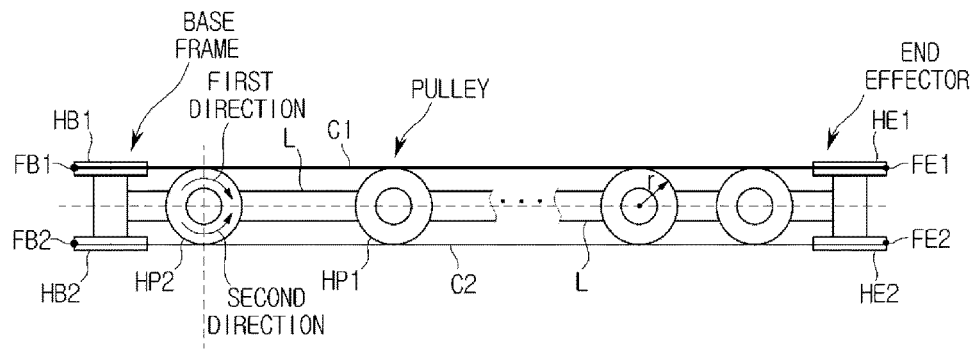
FIGS. 7A, 7B, and 7C are views illustrating a principle in which the pose of an end effector in a link unit having a multi-axis structure is maintained.
Figure 7B:
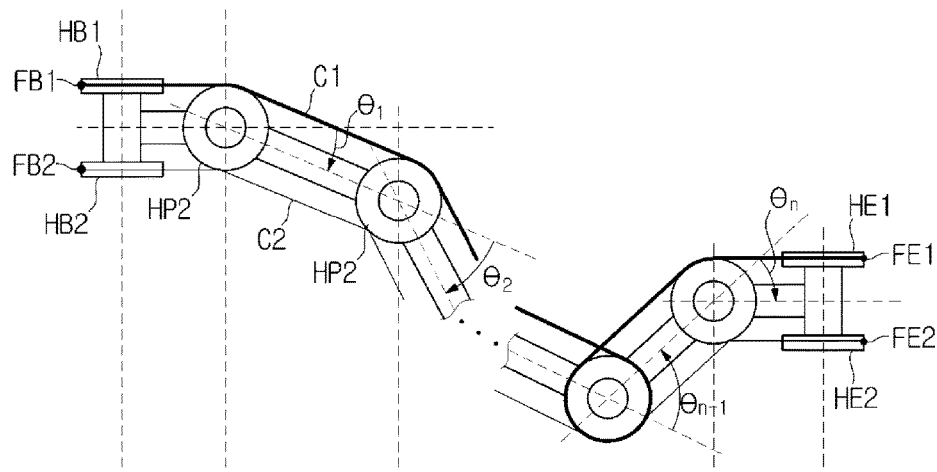
Figure 7C:
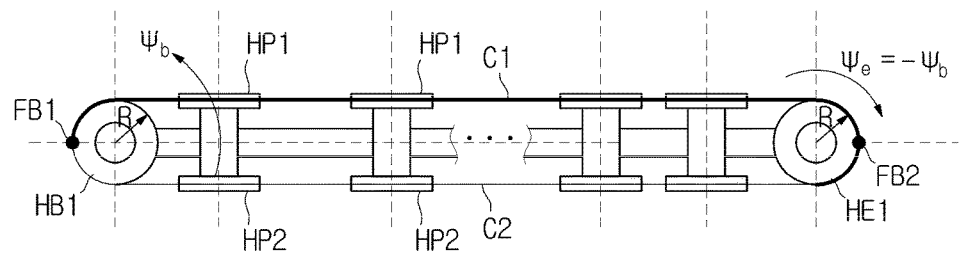

FIGS. 7A, 7B, and 7C are views illustrating a principle in which the pose of the end effector in the link unit is maintained. FIG. 7A is a side view illustrating arrangement of a base frame, at least one pulley, and an end effector. FIG. 7B is a side view illustrating rotation of at least one link. FIG. 7C is a plan view of FIG. 7B.

With reference to FIG. 7A, the base frame and the end effector are arranged in the same direction and separated from each other by a designated interval. In some example embodiments, the base frame and the end effector are arranged such that a rotary shaft of the base frame and a rotary shaft of the end effector are parallel with each other. The at least one pulley is arranged between the base frame and the end effector. The at least one pulley is arranged in the same direction, and a rotary shaft of each pulley is at an angle of 90 degrees with the rotary shaft of the base frame and the rotary shaft of the end effector. A link L is provided between the base frame and the pulley, between one pulley and another pulley, and between the pulley and the end effector. In some example embodiments, the pulley provided between one link and another link may be understood as a joint connecting the one link to the another link.

Each of the base frame, the end effector, and the at least one pulley has two grooves. Hereinafter, the two grooves will be referred to as "a first groove" and "a second groove". In the base frame, the diameter R×2 of the first groove HB1 and the diameter R×2 of the second groove HB2 are the same. In the end effector, the diameter R×2 of the first groove HE1 and the diameter R×2 of the second groove HE2 are the same. In the at least one pulley, the diameter r×2 of the first groove HP1 and the diameter r×2 of the second groove HP2 are the same.

In the base frame, the end effector, and the at least one pulley, the first groove and the second groove are separated by a designated interval. Hereinafter, the interval between the first groove and the second groove will be described in more detail.

With reference to FIG. 7A, it may be understood that the interval between the first groove HB1 and the second groove HB2 of the base frame is the same as the diameter r×2 of the first groove HP1 of the pulley and the diameter r×2 of the second groove HP2 of the pulley. Further, it may be understood that the diameter r×2 of the first groove HP1 of the pulley and the diameter r×2 of the second groove HP2 of the pulley is the same as the interval between the first groove HE1 and the second groove HE2 of the end effector.

With reference to FIG. 7C, it may be understood that the diameter R×2 of the first groove HB1 of the base frame and the diameter R×2 of the second groove HB2 of the base frame is the same as the interval between the first groove HP1 and the second groove HP2 of the pulley. Further, it may be understood that the interval between the first groove HP1 and the second groove HP2 of the pulley is the same as the diameter R×2 of the first groove HE1 of the end effector and the diameter R×2 of the second groove HE2 of the end effector.

In the state in which the at least one pulley is arranged between the base frame and the end effector, as exemplarily shown in FIG. 7A, one end of a first cable C1 is fixed to a cable fixing part FB1 provided in the first groove HB1 of the base frame. Thereafter, the first cable C1 is sequentially wound on the first groove HP1 of the at least one pulley. In some example embodiments, the first cable C1 is wound in a first direction. Thereafter, the other end of the first cable C1 is fixed to a cable fixing part FE1 provided in the first groove HE1 of the end effector.

Similar to the first cable C1, one end of a second cable C2 is fixed to a cable fixing part FB2 provided in the second groove HB2 of the base frame. Thereafter, the second cable C2 is sequentially wound on the second groove HP2 of the at least one pulley. In some example embodiments, the second cable C2 is wound in a second direction. Thereafter, the other end of the second cable C2 is fixed to a cable fixing part FE2 provided in the second groove HE2 of the end effector.

When the links are rotated in such a state, as exemplarily shown in FIG. 7B, the pulleys are rotated. As a result, the length of the first cable C1 wound on the first groove HP1 of each pulley and the length of the second cable C2 wound on the second groove HP2 of each pulley are changed. In accordance with some example embodiments, the varied lengths of the cables wound on each pulley may be compensated for by rotating the end effector. For example, the length of the first cable C1 wound on the first groove HP1 of each pulley may be compensated for by rotating the end effector. A rotating degree of the end effector may be calculated through Equation 1 below.

$$\sum_{i=1}^{n-1} r\theta_i + R\theta_n = 0 \quad \text{[Equation 1]}$$

As exemplarily shown in FIG. 7B, we assume that n pulleys are provided between the base frame and the end effector, the pulleys are numbered such that the pulley located close to the base frame is defined as a pulley i, and the link connected to the pulley i is defined as a link i (i=1, 2, . . . , n−1). Further, if we assume that the rotating angle of the link i is $\theta_i$, the length of the first cable C1 wound on the first groove HP1 of the pulley i is changed by $r\theta_i$. The length of the first cable C1 wound on the first groove HP1 of the pulley n is changed by $R\theta_n$. Equation 1 means that the end effector is rotated so that the sum of the changed lengths of the first cable C1 on the respective pulleys becomes 0.

If the links including a main link are rotated in the yaw direction, as exemplarily shown in FIG. 7C, the end effector is rotated in a direction opposite to the rotating direction of the links. As a result, the pose of the end effector is maintained ($\Psi_e = -\Psi_b$).

Figure 8:
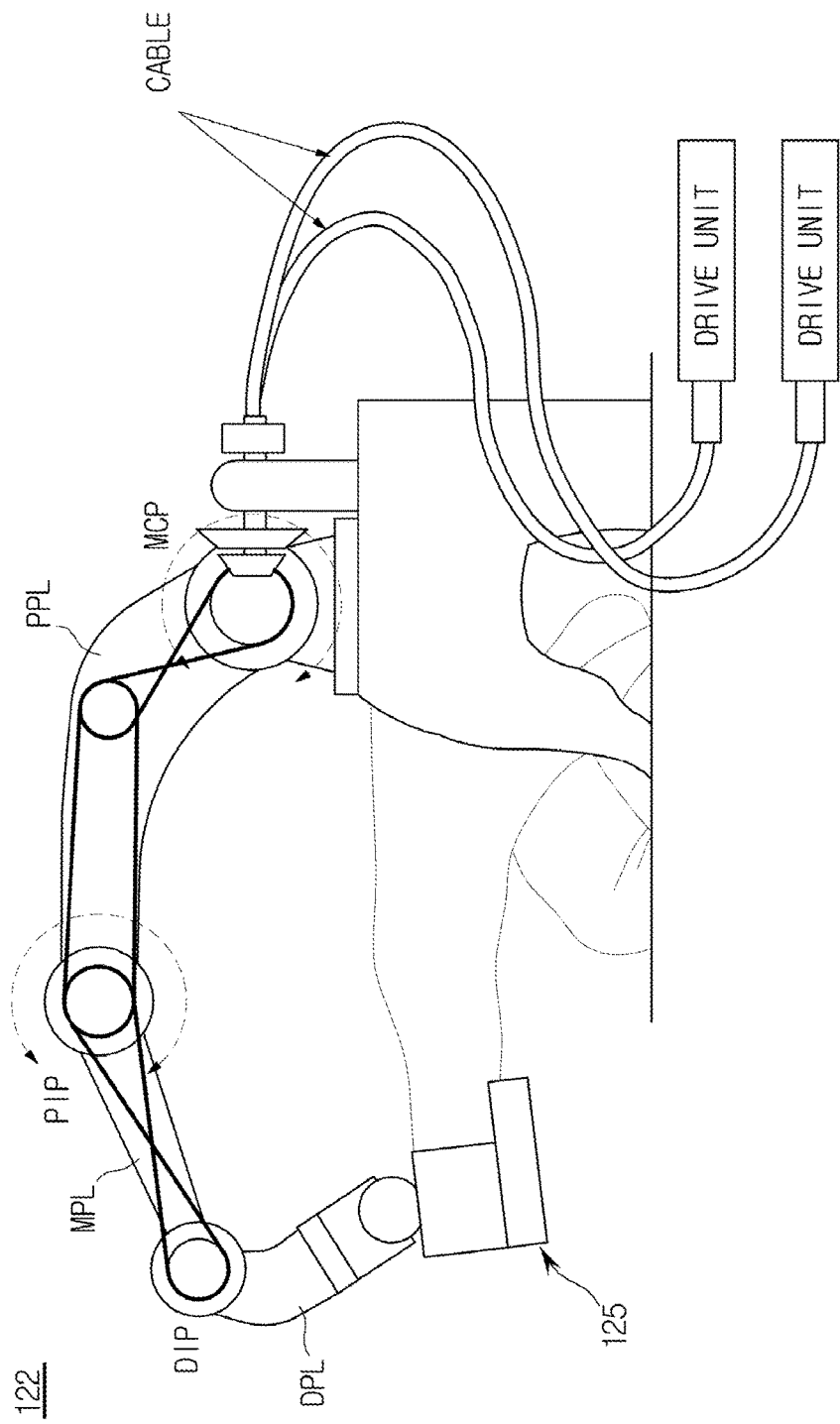
FIG. 8 is a view schematically illustrating the configuration of a multi-joint robot finger of a finger unit.

FIG. 8 is a view schematically illustrating the configuration of a multi-joint robot finger included in the handle unit 120. In more detail, FIG. 8 is a view schematically illustrating the configuration of a multi-joint robot finger 122 corresponding to the forefinger of a human hand.

As exemplarily shown in FIG. 8, the multi-joint robot finger 122 may include three links. The multi-joint robot finger 122 may include three links corresponding to the three phalanges forming a human finger. In more detail, the multi-joint robot finger 122 may include a proximal phalange link (PPL), a middle phalange link (MPL), and a distal phalange link (DPL).

A joint may be provided between one link and another link. Hereinafter, a joint provided at the end of the PPL is referred to as "a MCP joint". Further, a joint provided at a connection region between the PPL and the MPL is referred to as "a PIP joint". Further, a joint provided at a connection region between the MPL and the DPL is referred to as "a DIP joint".

In accordance with some example embodiments, the MCP joint, the PIP joint, and the DIP joint may be driven by three drive units. In accordance with some example embodiments, the MCP joint, the PIP joint, and the DIP joint may be driven, for example, by two drive units (underactuation). In some example embodiments, the joints may be driven by a smaller number of drive units than the number of the joints. In more detail, a cable connecting the DIP joint and the PIP joint may be connected to one drive unit, and a cable connecting the PIP joint and the MCP joint may be connected to the other drive unit. These drive units may be provided, for example, at the hand back part of the handle unit 120.

The tactile feedback actuator 125 may be provided at the end of the DPL of the multi-joint robot finger 122. An operator may move his/her finger under the condition that the end of his/her forefinger is inserted into the tactile feedback actuator 125. As the finger of the operator moves, the respective joints of the multi-joint robot finger 122 move.

The tactile feedback actuator 125 may be provided at other multi-joint robot fingers. For example, the tactile feedback actuator 125 may be provided at the end of the DPL of the multi-joint robot finger 123 corresponding to the middle finger of the human hand. However, the number and installation position of the tactile feedback actuators 125 are not limited thereto. For example, the tactile feedback actuator 125 may be provided at the end of the DPL of the multi-joint robot finger 121 corresponding to the thumb of the human hand.

In accordance with some example embodiments, movement of the tip of the multi-joint robot finger may be guided so as to follow a virtual trajectory. In some example embodiments, the virtual trajectory may vary according to the kind of a surgical tool 212a or 214a provided at the tip of the robotic surgery instrument 212 or 214 of the slave robot 200. Hereinafter, a more detailed description thereof will be given with reference to FIGS. 9A and 9B.

Figure 9A:
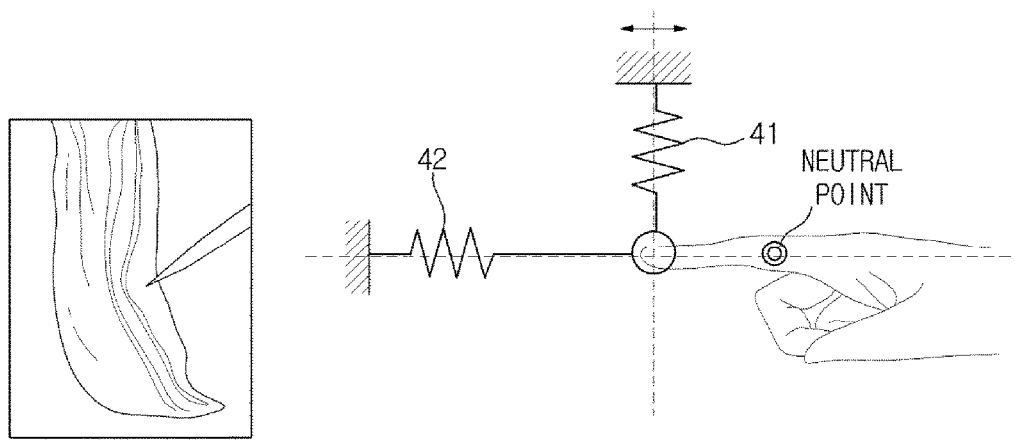
FIG. 9A is a view illustrating a virtual trajectory of the multi-joint robot finger and a guide method of the multi-joint robot finger, if a surgical tool provided at the end of the robotic surgical instrument is a palpation tool.

FIG. 9A is a view illustrating a virtual trajectory of the multi-joint robot finger and a guide method of the multi-joint robot finger, if the surgical tool 212a or 214a provided at the end of the robotic surgical instrument 212 or 214 is a palpation tool.

If the surgical tool 212a or 214a is a palpation tool, an operator may move his/her forefinger forward and backward under the condition that the positions of his/her thumb and middle finger are fixed, and thus move the palpation tool forward and backward. Therefore, if the surgical tool 212a or 214a is a palpation tool, a virtual trajectory of only the multi-joint robot finger 122 corresponding to the forefinger of a human hand may be generated.

Further, since the operator needs to move the palpation tool forward and backward for the purpose of palpation, the virtual trajectory of the palpation tool may be formed in the forward and backward direction. If it is assumed that there is a spring 42 connected in the horizontal direction and a spring 41 connected in the vertical direction to the end of the multi-joint robot finger 122 and stiffnesses of the springs 41 and 42 are adjusted, the end of the multi-joint robot finger 122 may be controlled so as to move along the virtual trajectory.

The control algorithm of FIG. 9A may be used in more general purpose control systems. For example, the control algorithm may be used in an aerospace vehicle (transport plane) so as to control takeoff, precision flying, and/or landing.

Figure 9B:
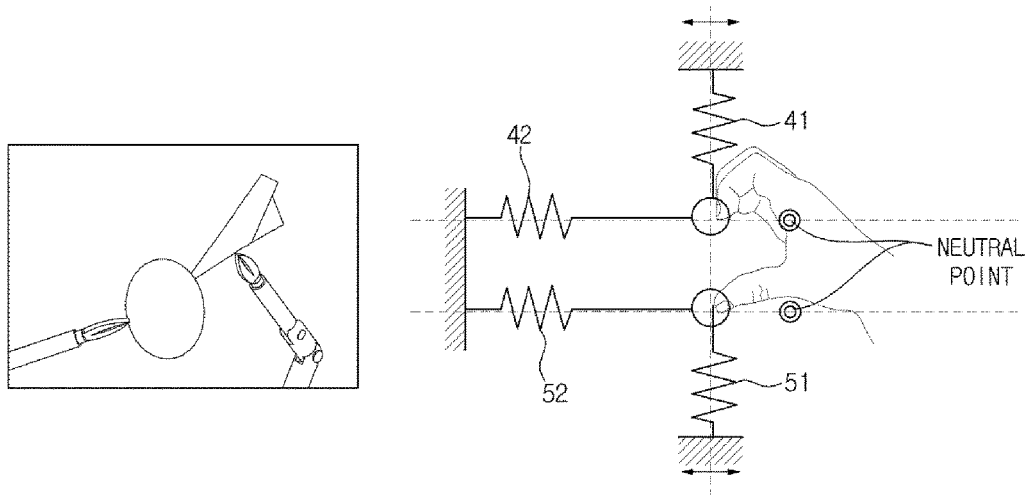
FIG. 9B is a view illustrating virtual trajectories of the multi-joint robot fingers and a guide method of the multi-joint robot fingers, if the surgical tool provided at the end of the robotic surgical instrument is a gripper.

FIG. 9B is a view illustrating virtual trajectories of the multi-joint robot fingers and a guide method of the multi-joint robot fingers, if the surgical tool 212a or 214a provided at the end of the robotic surgical instrument 212 or 214 is a gripper.

If the surgical tool 212a or 214a is a gripper, an operator may move his/her thumb and forefinger upward and downward under the condition that the position of his/her middle finger is fixed, and thus spread out both blades of the gripper or put the blades of the gripper together. Further, the operator may move his/her thumb and forefinger forward and backward together under the condition that the thumb and forefinger contact each other or are spread out, and thus move the gripper forward and backward. Therefore, if the surgical tool 212a or 214a is a gripper, virtual trajectories of only the multi-joint robot finger 121 corresponding to the thumb of a human hand and the multi-joint robot finger 122 corresponding to the forefinger of the human hand may be generated. Further, the virtual trajectory of the forefinger and the virtual trajectory of the thumb to spread out both blades of the gripper or to put the blades together may have a symmetrical relationship.

It may be assumed that there is a spring 42 connected in the horizontal direction and a spring 41 connected in the vertical direction to the end of the multi-joint robot finger 122 corresponding to the forefinger. Further, it may be assumed that there is a spring 52 connected in the horizontal direction and a spring 51 connected in the vertical direction to the end of the multi-joint robot finger 121 corresponding to the thumb. In such a state, if stiffnesses of the spring 41 connected in the vertical direction to the end of the multi-joint robot finger 122 corresponding to the forefinger and the spring 51 connected in the vertical direction to the end of the multi-joint robot finger 121 corresponding to the thumb are adjusted, both blades of the gripper may be controlled so as to be spread out or be put together along designated virtual trajectories. If stiffnesses of the spring 42 connected in the horizontal direction and the spring 41 connected in the vertical direction to the end of the multi-joint robot finger 122 corresponding to the forefinger are adjusted, and stiffnesses of the spring 52 connected in the horizontal direction and the spring 51 connected in the vertical direction to the end of the multi-joint robot finger 121 corresponding to the thumb are adjusted, the gripper may be controlled so as to move along designated virtual trajectories.

The control algorithm of FIG. 9B may be used in more general purpose control systems. For example, the control algorithm may be used in a system for handling hazardous materials so as to cause the system to sort, load, and/or unload the hazardous materials.

Figure 10:
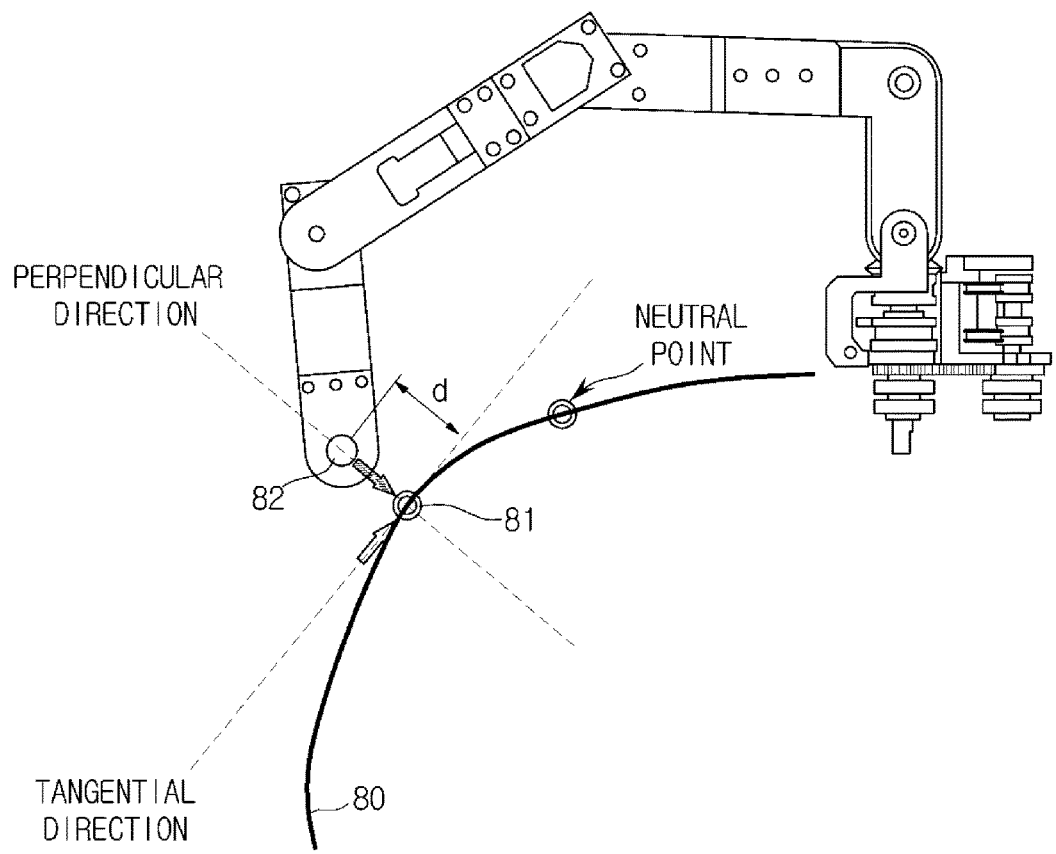
FIG. 10 is a view illustrating a movement control method of a handle unit.

FIG. 10 is a view illustrating a movement control method of the handle unit 120.

FIG. 10 illustrates the multi-joint robot finger 122 and a virtual trajectory 80 thereof. The virtual trajectory 80 serves to guide movement of the end of the multi-joint robot finger 122. Virtual trajectories 80 according to the kind of robotic surgical instruments 212 and 214 may be generated. In more detail, virtual trajectories 80 according to the kind of surgical tools 212a and 214a provided at the ends of the robotic surgical instruments 212 and 214 may be generated.

Assume that a current position 82 of the end of the multi-joint robot finger 122 deviates from the virtual trajectory 80, as exemplarily shown in FIG. 10. In this case, a point 81 on the virtual trajectory 80 having the shortest distance d from the current position 82 of the multi-joint robot finger 122 is detected. Thereafter, the end of the multi-joint robot finger 122 may be guided so as to follow the virtual trajectory 80 by adjusting force in the perpendicular direction, applied to the detected point 81 from the current position 82 of the end of the multi-joint robot finger 122, and force in the tangential direction at the detected point 81.

If the end of the multi-joint robot finger 122 is located on the virtual trajectory 80 in FIG. 10, resistance in the perpendicular direction of the virtual trajectory 80 is raised and resistance in the tangential direction of the virtual trajectory 80 is lowered at the current position of the end of the multi-joint robot finger 122. Thereby, deviation of the end of the multi-joint robot finger 122 from the virtual trajectory 80 in the perpendicular direction may be prevented, and the end of the multi-joint robot finger 122 may move in the tangential direction of the virtual trajectory 80. Thus, when the end of the multi-joint robot finger 122 deviates from the virtual trajectory 80, a control signal to restore the end of the multi-joint robot finger 122 to the virtual trajectory 80 is generated. When such a control signal is generated, the end of the multi-joint robot finger 122 may be guided so as to follow the virtual trajectory 80.

Figure 11:
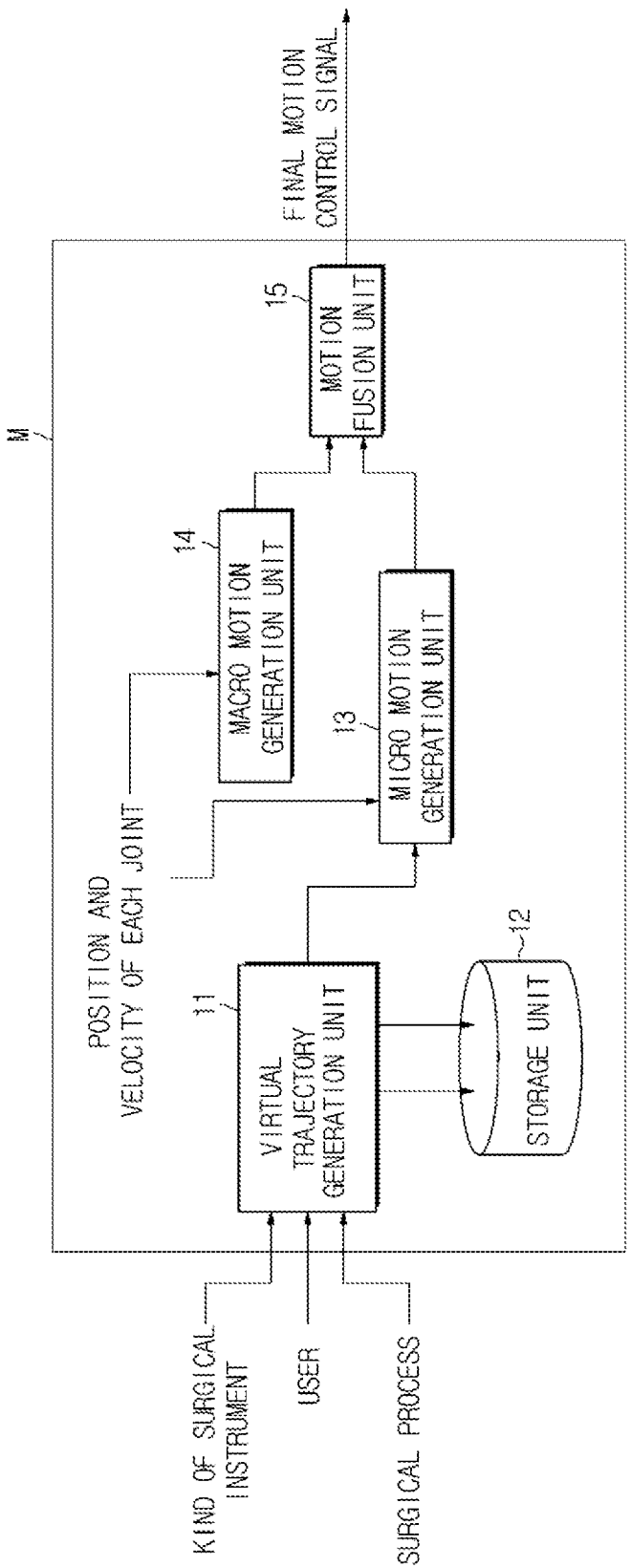
FIG. 11 is a view exemplarily illustrating a control configuration of the master device.

FIG. 11 is a view exemplarily illustrating a control configuration of the master device M.

As exemplarily shown in FIG. 11, the master device M may include a storage unit 12, a virtual trajectory generation unit 11, a micro motion generation unit 13, a macro motion generation unit 14, and a motion fusion unit 15.

The storage unit 12 may store virtual trajectories 80 of the multi-joint robot fingers 121, 122, and 123. The virtual trajectories 80 may be generated according to the kind of robotic surgical instruments 212 and 214. In more detail, different virtual trajectories 80 may be generated according to the kind of surgical tools 212a and 214a provided at the ends of the robotic surgical instruments 212 and 214. For example, if the surgical tool 212a or 214a is a palpation tool, a virtual trajectory 80 of only the multi-joint robot finger 122 corresponding to the forefinger of a human hand (except for the thumb and the middle finger of the human hand) may be generated. In some example embodiments, the virtual trajectory 80 may be generated in consideration of motion of the palpation tool.

If the surgical tool 212a or 214a is a gripper, virtual trajectories 80 of only the multi-joint robot fingers 121 and 122 corresponding to the thumb and the forefinger of a human hand (except for the middle finger of the human hand) may be generated. The virtual trajectory 80 of the multi-joint robot finger 121 corresponding to the thumb may be generated in consideration of motion of the thumb of an operator. The virtual trajectory 80 of the multi-joint robot finger 122 corresponding to the forefinger may be generated in consideration of motion of the forefinger of the operator.

The virtual trajectory generation unit 11 may receive at least one of information regarding the kind of robotic surgical instruments 212 and 214, information regarding the operator, and information regarding a surgical process from the operator or an external device. In more detail, the virtual trajectory generation unit 11 may receive information regarding the kind of robotic surgical instruments 212 and 214, and search virtual trajectories corresponding to the received kind of robotic surgical instruments 212 and 214 in the storage unit 12. Further, the virtual trajectory generation unit 11 may amend the searched virtual trajectories based on at least one of information regarding the operator and information regarding the surgical process.

The information regarding the kind of robotic surgical instruments 212 and 214 may mean information regarding the kind of surgical tools 212a and 214a provided at the ends of the robotic surgical instruments 212 and 214. The information regarding the operator may exemplarily include the sex of the operator and the finger lengths of the operator. The information regarding the surgical process may exemplarily include the kind of surgery.

Although the same robotic surgical instrument is used, lengths of fingers may vary according to operators. Therefore, if virtual trajectories are amended based on the finger lengths of an operator and the multi-joint robot fingers are guided so as to move along the amended virtual trajectories, movement of the multi-joint robot fingers may be more finely controlled, as compared to the case in which virtual trajectories are not amended.

If finger length information of an operator is not input and only the sex of the operator is received, virtual trajectories may be generated based on the mean finger length information according to the sex.

Further, although the same robotic surgical instrument is used, virtual trajectories applied to the robotic surgical instrument may vary according to surgical processes. Therefore, if information of a surgical process is received, the virtual trajectories are amended based on the received information of the surgical process, and the multi-joint robot fingers are guided so as to move along the amended virtual trajectories, so that unnecessary movement of the robotic surgical instrument may be prevented.

The virtual trajectories retrieved from the storage unit 12 and the virtual trajectories amended based on the received information may be provided to the micro motion generation unit 13.

The micro motion generation unit 13 may receive information regarding positions and velocities of the respective joints of the multi-joint robot fingers, and amend the virtual trajectories. The micro motion generation unit 13 may generate a control signal to control movement of the ends of the multi-joint robot fingers along the amended virtual trajectories.

The macro motion generation unit 14 may receive rotation information of the wrist support units 140 and/or position information of the wrist support units 140. The macro motion generation unit 14 may generate a control signal to control the poses of the robotic surgical instruments 212, 214, and 216 based on the rotation information of the wrist support units 140. Further, the macro motion generation unit 14 may generate a control signal to control the positions of the robotic surgical instruments 212, 214, and 216 based on the position information of the wrist support units 140.

The motion fusion unit 15 may generate a final motion control signal through fusion between the control signal generated by the micro motion generation unit 13 and the control signal generated by the macro motion generation unit 14. In some example embodiments, the motion fusion unit 15 may generate the final motion control signal by applying weights to the control signal generated by the micro motion generation unit 13 and the control signal generated by the macro motion generation unit 14. The weights applied to the respective control signals may be understood as scaling factors to scale the respective control signals. The scaling factors may be set in advance by the operator. The final motion control signal generated in such a manner is a signal to control the motion of the robotic surgical instruments 212, 214, and 216, and may be transmitted to the slave robot 200 through a communication unit (not shown).

The algorithms discussed in this application (e.g., required to control the surgical robots and methods) may be used in more general purpose apparatuses and/or methods of controlling apparatuses. For example, the algorithms may be used in intelligent robots for handling equipment and materials and/or for controlling such intelligent robot so as to allow safe movement, packaging, and/or shipment of the equipment and materials.

The methods described above may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' may be interpreted as software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiment, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to surgical robots and methods, those skilled in the art will appreciate that some example embodiments may be applied to other types of systems and methods, such as systems not used in the medical field (e.g., aerospace teleoperation systems and methods, apparatuses and methods for handling hazardous materials, patrol apparatuses and methods, military apparatuses and methods), humanoid apparatuses and methods, or more general purpose control systems and methods. Those skilled in the art will appreciate that the surgical robots and methods described in this application have a myriad of practical uses.

Although some example embodiments of the present disclosure have been shown and described, it would be appreciated by those skilled in the art that changes may be made in these example embodiments without departing from the principles and spirit of the invention, the scope of which is defined in the claims and their equivalents.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A master device, comprising:
 a plurality of handle units, each of the plurality of handle units including at least one multi-joint robot finger, the at least one multi-joint robot finger configured to control a respective instrument of a plurality of instruments on a robot arm of a slave device; and
 at least one processor configured to execute computer readable instructions to,
  generate a first control signal, the first control signal configured to guide a distal end of the at least one multi-joint robot finger along a first virtual trajectory of a plurality of virtual trajectories, the distal end of the at least one multi-joint robot finger being guided along the first virtual trajectory by adjusting a force applied to a point on the first virtual trajectory in a perpendicular direction.

2. The master device according to claim 1, wherein at least one processor is further configured to execute the computer readable instructions to,
 search the first virtual trajectory from the plurality of virtual trajectories based on the respective instrument on the robot arm, the plurality of virtual trajectories stored in a memory.

3. The master device according to claim 2, wherein the at least one processor is further configured to execute the computer readable instructions to,
 generate a second virtual trajectory from the plurality of trajectories based on information received by the at least one processor, the information includes at least one of (i) information regarding an operator of the master device, and (ii) information regarding a process.

4. The master device according to claim 3, wherein the at least one processor is further configured to execute the computer readable instructions to,
 generate a second control signal to move the distal end of the at least one multi-joint robot finger along the second virtual trajectory.

5. The master device according to claim 1, further comprising:
 a plurality of wrist support units, a respective one of the plurality of wrist support units configured to rotate a respective one of the plurality of handle units about at least one of an x-axis, a y-axis, and a z-axis; and
 a plurality of link units, a respective one of the plurality of link units connected to the respective one of the plurality of wrist support units, and the respective one of the link units configured to translate the respective one of wrist support units.

6. The master device for according to claim 5, wherein the at least one processor is further configured to execute the computer readable instructions to,
 generate a second control signal to control a pose of the respective instrument based on rotation information of the respective one of the plurality of wrist support units, and
 generate a third control signal to control a position of the respective instrument based on position information of the respective one of the plurality of wrist support units.

7. The master device for according to claim 6, wherein the at least one processor is further configured to execute the computer readable instructions to,
 generate a final motion control signal to control motion of the respective instrument by combining the second and third control signals with a fourth control signal, the fourth control signal configured to move the distal end of the at least one multi-joint robot finger along a second virtual trajectory.

8. The master device according to claim 7, wherein the at least one processor is further configured to execute the computer readable instructions to,
 apply weights to the second, third and fourth control signals.

9. The master device according to claim 5, wherein each of the plurality of link units comprises:
 a first link on the respect one of the plurality of wrist support units;
 a second link connected to a first end of the first link;
 a third link connected to a first end of the second link; and
 fourth link connected to a first end of the third link and a second end of the first link,
 wherein the first link, the second link, the third link, and the fourth links are configured to form a parallelogram structure.

10. The master device according to claim 9, wherein each of the plurality of link units further comprises:
 a first pulley at one side of the first link;
 a second pulley on a first rotary shaft with which the first link and the fourth links are combined;
 a third pulley on a second rotary shaft with which the third link and the fourth links are combined;
 a first cable wound on a first groove of the first pulley, a first groove of the second pulley, and a first groove of the third pulley; and
 a second cable wound on a second groove of the first pulley, a second groove of the second pulley, and a second groove of the third pulley.

11. The master device according to claim 10, wherein
the first cable includes a first end fixed to a cable fixing part in the first groove of the first pulley,
the first cable is wound on the first groove of the second pulley in a first direction,
a second end of the first cable is fixed to a cable fixing part in the first groove of the third pulley,
the second cable includes a first end fixed to a cable fixing part in the second groove of the first pulley,
the second cable is wound on the second groove of the second pulley in a second direction, and
the second cable includes a second end fixed to a cable fixing part in the second groove of the third pulley.

12. The master device according to claim 11, wherein the respective one of the plurality of link units is configured to,
maintain a pose of the respective one of the plurality of wrist support units by regulating a length of the first cable and a length of the second cable according to rotation of the first, second, third and fourth links.

13. The master device according to claim 1, wherein when a position of the distal end of the at least one multi-joint robot finger deviates from the first virtual trajectory, the at least one processor is further configured to execute the computer readable instructions to,
adjust an intensity of force applied in a tangential direction at the point on the first virtual trajectory, the point having a shortest distance from the position of the distal end of the at least one multi-joint robot finger.

14. A method of controlling a master device for surgical robots, the master device including a plurality of handle units, each of the plurality of handle units including at least one multi-joint robot finger configured to control a respective robotic surgical instrument of a plurality of robotic surgical instruments on a robot arm of a slave device, the method comprising:
generating a first virtual trajectory of an end of the at least one multi-joint robot finger;
generating a first control signal to guide a distal end of the at least one multi-joint robot finger along the first virtual trajectory of a plurality of virtual trajectories, the distal end of the at least one multi-joint robot finger being guided along the first virtual trajectory by adjusting a force applied to a point on the first virtual trajectory in a perpendicular direction; and
controlling motion of the at least one multi-joint robot finger according to the first control signal.

15. The method according to claim 14, further comprising:
searching the first virtual trajectory from the plurality of virtual trajectories based on the respective robotic surgical instrument on the robot arm, the plurality of virtual trajectories stored in a memory; and
generating a second virtual trajectory from the plurality of virtual trajectories based on information received by at least one processor, the information includes at least one of (i) information regarding an operator the master device, and (ii) information regarding a surgical process.

16. The method according to claim 14, further comprising:
generating a second control signal to control a pose of the respective robotic surgical instrument based on rotation information of a respective one of the a plurality of wrist support units, the respective one of the plurality of wrist support units configured to rotate a respective one of the plurality of handle units in a designated axis direction; and
generating a third control signal to control a position of the respective robotic surgical instrument based on position information of the respective one of the plurality of wrist support units.

17. The method according to claim 14, further comprising:
when a position of the distal end of the at least one multi-joint robot finger deviates from the first virtual trajectory;
adjusting an intensity of force applied in a tangential direction at the point on the first virtual trajectory, the point having a shortest distance from the position of the distal end of the at least one multi-joint robot finger.

18. A master device, comprising:
a first unit that including at least one multi-joint robot finger on a robot arm of a slave device; and
at least one processor configured to execute computer readable instructions to,
generate a first control signal, the first control signal configured to guide a distal end of the at least one multi-joint robot finger along a virtual trajectory, the distal end of the at least one multi-joint robot finger being guided along the virtual trajectory by adjusting a force applied to a point on the virtual trajectory in a perpendicular direction.

19. The master device according to claim 18, further comprising:
a second unit including a plurality of wrist support units, a respective one of the plurality of wrist support units in the second unit is configured to rotate the first unit about at least one of an x-axis, a y-axis, and a z-axis.

20. The master device according to claim 19, wherein the at least one processor is further configured to execute the computer readable instructions to,
generate a second control signal to control the robot arm based on rotation information of the second unit.

21. The master device according to claim 20, wherein the at least one processor is further configured to execute the computer readable instructions to,
generate a third control signal to control the robot arm based on the first and second control signals.

22. The master device according to claim 19, wherein the at least one processor is further configured to execute the computer readable instructions to,
generate a second control signal to control the robot arm based on position information of the second unit.

23. The master device according to claim 22, wherein the at least one processor is further configured to execute the computer readable instructions to,
generate a third control signal to control the robot arm based on the first and second control signals.

24. The master device according to claim 19, wherein the at least one processor is further configured to execute the computer readable instructions to,
generate a second control signal to control the robot arm based on rotation information and position information of the second unit.

* * * * *